(12) United States Patent
Chang

(10) Patent No.: US 11,492,598 B2
(45) Date of Patent: Nov. 8, 2022

(54) CELL CULTURE SUBSTRATES, METHODS AND USES THEREOF

(71) Applicant: Academia Sinica, Taipei (TW)

(72) Inventor: Ying-Chih Chang, Atherton, CA (US)

(73) Assignee: ACADEMIA SINICA, Taipei (TW)

(*) Notice: Subject to any disclaimer, the term of this patent is extended or adjusted under 35 U.S.C. 154(b) by 0 days.

(21) Appl. No.: 17/566,179

(22) Filed: Dec. 30, 2021

(65) Prior Publication Data
US 2022/0204944 A1 Jun. 30, 2022

Related U.S. Application Data

(60) Provisional application No. 63/252,268, filed on Oct. 5, 2021, provisional application No. 63/132,934, filed on Dec. 31, 2020.

(51) Int. Cl.
*C12N 5/09* (2010.01)
*G01N 33/50* (2006.01)

(52) U.S. Cl.
CPC ....... *C12N 5/0693* (2013.01); *G01N 33/5011* (2013.01); *G01N 33/5088* (2013.01); *C12N 2513/00* (2013.01); *C12N 2533/32* (2013.01); *C12N 2533/40* (2013.01); *C12N 2537/10* (2013.01); *C12N 2539/10* (2013.01)

(58) Field of Classification Search
CPC .............. C12N 5/0693; C12N 2513/00; C12N 2533/32; C12N 2533/40; C12N 2537/10; G01N 33/5011; G01N 33/5088
See application file for complete search history.

(56) References Cited

U.S. PATENT DOCUMENTS

| | | | |
|---|---|---|---|
| 2011/0151564 A1 | 6/2011 | Menu et al. | |
| 2013/0210140 A1 | 8/2013 | Burns et al. | |
| 2014/0093962 A1 | 4/2014 | Ingram et al. | |
| 2020/0095526 A1 | 3/2020 | Rothbauer et al. | |

OTHER PUBLICATIONS

Tu et al., Surface modification of poly(dimethylsiloxane) and its applications in microfluidics-based biological analysis. Rev Anal Chem 2012; 31(3-4):177-192. (Year: 2012).*
Richert et al., pH dependent growth of poly(L-lysine)/poly(L-glutamic) acid multilayer films and their cell adhesion properties. Surface Science Oct. 2004; 570(1-2): 13-29 (Year: 2004).*
Chen et al., Drug cytotoxicity and signaling pathway analysis with three-dimensional tumor spheroids in a microwell-based microfluidic chip for drug screening. Analytica Chimica Acta, 2015; 898: 85-92. (Year: 2015).*
Chen et al., High-throughput single-cell derived sphere formation for cancer stem-like cell identification and analysis. Scientific Reports, Jun. 13, 2016; 6: 27301 (Year: 2016).*
Arias, Carlos, J., et al., "Quasi-Spherical Cell Clusters Induced by a Polyelectrolyte Multilayer," American Chemical Society, ACS Publications 2015, Langmuir, vol. 31, pp. 6436-6446.

(Continued)

*Primary Examiner* — Kara D Johnson
(74) *Attorney, Agent, or Firm* — Foley & Lardner LLP

(57) ABSTRACT

The present disclosure provides a substrate for cell culture. Systems comprising the substrate, and methods for using and manufacturing the substrate are also disclosed herein.

30 Claims, 10 Drawing Sheets

(56) References Cited

OTHER PUBLICATIONS

Detzel, Ph.D., Christopher, J., et al., "Polyelectrolyte Multilayers in Tissue Engineering," Tissue Engineering: Part B, vol. 17, No. 2, 2011, DOI:10.1089/ten.teb.2010.0548, pp. 101-113.

Dou, Xiaoqiu, et al., Three-Dimensional Microstructured Poly(vinyl alcohol) Hydrogel Platform for the Controlled Formation of Multicellular Cell Spheroids, 2018, Biomacromolecules, 19(1):158-166.

Facca, S., et al., "Active multilayered capsules for in vivo bone formation," 2010, PNAS, 107(8):3406-3411.

International Search Report dated Apr. 29, 2022 issued in International Application No. PCT/US2021/065694, 4 pages.

International Search Report dated May 2, 2022 issued in International Application No. PCT/US2021/065683, 3 pages.

Kidambi, Srivatsan, et al., "Cell Adhesion on Polyelectrolyte Multilayer Coated Polydimethylsiloxane Surfaces with Varying Topographies," Tissue Engineering, vol. 13, No. 8, 2007, DOI: 10.1089/ten.2006.0151, pp. 2105-2117.

Non-Final Office Action on U.S. Appl. No. 17/566,166 dated May 20, 2022.

Takenaka, Chiemi, "Controlled Growth and the Maintenance of Human Pluripotent Stem Cells by Cultivation with Defined Medium on Extracellular Matrix-Coated Micropatterned Dishes," 2015, Plos One, 10(6): e0129855: 1-13.

Tsai, Hsuan-Ang, et al., "Selection, Enrichment, and Maintenance of Self-Renewal Liver Stem/Progenitor Cells Utilizing Polypeptide Polyelectrolyte Multilayer Films," Biomacromolecules 2010, vol. 11, pp. 994-1001.

Tsai, Hsuan-Ang, et al., "Use of Surface Properties to Control the Growth and Differentiation of Mouse Fetal Liver Stem/Progenitor Cell Colonies," Biomacromolecules 2012 American Chemical Society, vol. 13, pp. 3483-3493.

Written Opinion of the International Searching Authority dated Apr. 29, 2022 issued in International Application No. PCT/US2021/065694, 5 pages.

Written Opinion of the International Searching Authority dated May 2, 2022 issued in International Application No. PCT/US2021/065683, 5 pages.

Wu, Dapeng, et al., "Multilayer poly(vinyl alcohol)-adsorbed coating on poly(dimethylsiloxane) microfluidic chips for biopolymer separation," Electrophoresis, 2005, vol. 26, pp. 211-218.

Final Office Action on U.S. Appl. No. 17/566,166 dated Aug. 19, 2022.

Trantidou, Tatiana, et al., "Hydrophilic surface modification of PDMS for droplet microfluidics using a simple, quick, and robust method via PVA deposition," 2017, Microsystems & Nanoengineering, 3:16091 (Year: 2017).

\* cited by examiner

CELL CULTURE SUBSTRATES, METHODS AND USES THEREOF

CROSS-REFERENCE TO RELATED APPLICATIONS

This application claims priority to and the benefit of U.S. Provisional Patent Application No. 63/132,934, filed Dec. 31, 2020 and U.S. Provisional Patent Application No. 63/252,268, filed Oct. 5, 2021, the disclosure of which is hereby incorporated herein by reference in its entirety.

BACKGROUND OF THE INVENTION

The interest in 3D spheroid models is growing among researchers, from basic science to preclinical drug discovery applications, including studies in tumor biology, neurodegenerative diseases, and drug toxicity. Three-dimensional (3D) cell culture methods are increasingly used to generate complex tissue or tumor models.

There is a lot of variation in the spheroids formed using 3D cell culture methods and products available on the market, and this may impact their read-out. For instance, the widely used non-adherent techniques for 3D cell culture, including Ultra Low Attachment (ULA) plate and hanging drop method, have not proven suitable because these methods usually generate spheroids via cell agglomeration. Such spheroids generally maintain their original heterogeneity and harbor multiple cells with various characteristics, requiring a better understanding of cellular heterogeneity. When tens-of-thousands cells are aggregated into a spheroid (i.e., a mass with spherical shape), an extensive central necrotic core may form over a few hours due to the lack of nutrient and oxygen penetration, and thus hinders cell proliferation. Extended central necrosis is a rare phenomenon in real cancers.

Alternatively, Matrigel is a commonly used embedded substrate for tissue-based cell growth, such as organoid formation. But out of focus, inefficient compound diffusion, and difficulty in sample isolation limits its application for ex vivo 3D spheroid-based applications.

Standardizing spheroid formation is critical to generating uniform 3D cell culture and obtaining reproducible results from spheroid-based assays and drug screening. Therefore, there is a need for the development of new cell culture systems and methods that can reliably form single cell-derived spheroids.

SUMMARY OF THE INVENTION

The present disclosure provides a cell culture substrate (hereinafter referred to as a "substrate") for use in culturing cells. The substrate provided herein comprises an elastomer membrane coated with polyelectrolyte multilayers and an absorbent polymer. The coating described herein is advantageous for hydration preservation. It can prevent the cell culture substrate from undesirable surface cracks caused by prolonged storage at ambient temperature. Also provided is a cell culture system comprising the substrate. Uses and methods of preparing the substrate and cell culture systems comprising such are provided as well.

Accordingly, one aspect of the present disclosure provides a substrate in a form of a multilayered membrane comprises polyelectrolyte multilayers, an absorbent polymer, and an elastomer membrane, in which the absorbent polymer is deposited on top of the elastomer membrane, and the polyelectrolyte multilayers are deposited on top of the absorbent polymer. The polyelectrolyte in direct contact with the absorbent polymer may be a polycation or a polyanion. The outermost layer of the substrate may be a polycation or a polyanion.

In some embodiments, the elastomer described herein is a silicone elastomer. In preferred embodiments, the silicone elastomer is polydimethylsiloxane (PDMS).

Suitable absorbent polymers include, but are not limited to, poly(vinyl alcohol) (PVA), poly(ethylene glycol) (PEG), PEG-acrylate, polyvinylpyrrolidone (PVP), polyethyleneimine (PEI), poly-L-lactide (PLLA), poly-D-lactide (PDLA), poly(L-lactide-co-D,L-lactide) (PLDLLA), poly (glycolic acid) (PGA), poly(lactic-co-glycolic acid) (PL-co-GA), poly(methyl methacrylate) (PMMA), poly(hydroxyethyl methacrylate) (p-HEMA) and derivatives thereof.

In some embodiments, the absorbent polymer is PVA, PEG, PVP, PEI, PMMA or a derivative thereof. In some embodiments, the absorbent polymer is PVA. In some embodiments, the absorbent polymer is PEG or PEG-acrylate such as PEGMA, PEGDMA or PEGDA. In some embodiments, the absorbent polymer is PLA or a derivative such as PLLA, PDLA or PLDLLA. In some embodiments, the absorbent polymer is PGA or a derivative such as PLGA. In some embodiments, the absorbent polymer is PMAA or a derivative such as pHEMA.

In certain embodiments, the volume of the absorbent polymer is 0.01-10% of the total volume of the surface coating.

The polyelectrolyte multiplayers described herein comprise at least one layer pair (referred as "bilayer") comprising a cationic polyelectrolyte (referred as "polycation") and an polyelectrolyte (referred as "polyanion"). In some embodiments, the polycation is a poly(amino acid). In some embodiments, the polyanion is a poly(amino acid). In some embodiments, the polycation and the polyanion are poly (amino acid)s. The poly(amino acid)s described herein may comprise L and/or D amino-acid forms. As described herein, the polyelectrolyte multiplayers can be formed by depositing polycations and polyanions in an alternative fashion via layer-by-layer assembly.

In some embodiments, the polyelectrolyte multilayers having a formula of (polycation/polyanion)$_n$ comprise n bilayers of polycations and polyanions, wherein n is an integer number ranging from 1 to 30. In some embodiments, n is 1, 2, 3, 4, 5, 6, 7, 8, 9, 10, 11, 12, 13, 14, 15, 16, 17, 18, 19 or 20. In some embodiments, n is in a range of 1-10, 1-8, 1-5, 3-20, 5-20, 10-20, 11-19, 12-18, 13-17, or 14-16.

In some embodiments, the polyelectrolyte multilayers having a formula of polyanion(polycation/polyanion)$_n$ comprise n+1 layers of polyanions and n layers of polycations, wherein n is an integer number ranging from 1 to 30. In some embodiments, n is 1, 2, 3, 4, 5, 6, 7, 8, 9, 10, 11, 12, 13, 14, 15, 16, 17, 18, 19 or 20. In some embodiments, n is in a range of 1-10, 1-8, 1-5, 3-20, 5-20, 10-20, 11-19, 12-18, 13-17, or 14-16.

In some embodiments, the polyelectrolyte multilayers having a formula of polycation(polyanion/polycation)$_n$ comprise n+1 layers of polycations and n layers of polyanions, wherein n is an integer number ranging from 1 to 30. In some embodiments, n is 1, 2, 3, 4, 5, 6, 7, 8, 9, 10, 11, 12, 13, 14, 15, 16, 17, 18, 19 or 20. In some embodiments, n is in a range of 1-10, 1-8, 1-5, 3-20, 5-20, 10-20, 11-19, 12-18, 13-17, or 14-16.

In some embodiments, the polycation is poly(L-lysine) (PLL), poly(L-arginine) (PLA), poly(L-ornithine) (PLO), poly(L-histidine) (PLH), or a combination thereof. In a preferred embodiment, the polycation is PLL.

In preferred embodiments, the polyanion is poly(L-glutamic acid) (PLGA), poly(L-aspartic acid) (PLAA), or a combination thereof. In a preferred embodiment, the polyanion is PLGA.

In some embodiments, said polyelectrolyte multilayers comprise at least one layer pair (i.e., bilayer) of polycation/polycation selecting from the group consisting of PLL/PLGA, PLL/PLAA, PLA/PLGA, PLA/PLAA, PLO/PLGA, PLO/PLAA, PLH/PLGA, PLH/PLAA, and a combination thereof.

In some embodiments, the bilayer described herein comprises a combination of PLL and PLGA. In some embodiments, the bilayer described herein comprises a combination of PLO and PLGA. In some embodiments, the bilayer described herein comprises a combination of PLH and PLGA. In some embodiments, the bilayer described herein comprises a combination of PLA and PLGA.

In some embodiments, the bilayer described herein comprises a combination of PLL and PLAA. In some embodiments, the bilayer described herein comprises a combination of PLO and PLAA. In some embodiments, the bilayer described herein comprises a combination of PLH and PLAA. In some embodiments, the bilayer described herein comprises a combination of PLA and PLAA.

In some embodiments, the polyelectrolyte multilayers described herein may have a thickness ranging from 30 nm to 30 μm. In some embodiments, the surface coating has a thickness ranging from 100 nm to 20 μm. In some embodiments, the surface coating has a thickness of 200, 400, 600 or 800 nm. In some embodiments, the surface coating has a thickness of 1, 5, 10, 15 or 20 μm.

Compared with conventional culture methods, the surface coating of the present disclosure offers an improved proliferation rate for a variety of cells including, but not limited to, tumor cells, pluripotent and multipotent stem and progenitor cells, hematopoietic cells and immune cells. In addition, the surface coating with elevated water retention offers an advantage to prevent the surface coating from undesirable surface cracks caused by dehydration due to prolonged storage at ambient temperature.

In another aspect, the present invention provides methods for preparing the substrate of the present disclosure. In some embodiments, the method described herein comprises the steps of: (a) providing a support; (b) applying an elastomer onto a surface of the support; (c) applying an absorbent polymer onto the elastomer; (d) sequentially depositing on the absorbent polymer alternating layers of polycations and polyanions to form a multilayered membrane; and (e) delaminating the multilayered membrane from the support to obtain a substrate.

In some embodiments, the elastomer is PDMS. In some embodiments, the PDMS comprises a hydrophobic surface. In some embodiments, the method described herein comprises the steps of: (a) providing a PDMS membrane having a hydrophobic surface; (b) modifying the hydrophobic surface of PDMS with a treatment; (c) applying an absorbent polymer to the modified surface of PDMS; and (d) sequentially depositing on the absorbent polymer alternating layers of polyelectrolytes, thereby a coated PDMS membrane is obtained.

In some embodiments, the treatment described herein is a plasma treatment, corona discharge or UV ozone treatment. In some embodiments, the hydrophobic surface of PDMS is irradiated or hydrophilized after the treatment. In some embodiments, the PDMS surface is hydrophilized after applying the absorbent polymer to the modified surface of PDMS. In some embodiments, the hydrophobic surface of PDMS is converted to a hydrophilic surface after applying PVA to the modified surface of PDMS.

In some embodiments, the hydrophobic surface of PDMS is modified by hydrosilylation. In some embodiments, the hydrosilylation is a platinum-catalyzed hydrosilylation. In some embodiments, the PDMS surface is hydrophilized after applying a PEG-acrylate to the surface-modified PDMS. In some embodiments, the absorbent polymer (e.g., PEG or PEG-acrylate) is covalently linked (i.e., conjugated) to the PDMS surface. A cross-linking agent may be used to facilitate the crosslinking of the absorbent polymer and the elastomer. Exemplary cross-linking agents include, but are not limited to, maleic acid, formaldehyde, glutaraldehyde, butanal (butyraldehyde), sodium borate, or a combination thereof.

In some embodiments, the PDMS is free of crosslinks.

The support described herein can be made of any suitable material. Exemplary materials include, but are not limited to, metal, glass and silicon dioxide. In some embodiments, the support is made of glass or silicon wafer.

In another aspect, the present invention provides a cell culture article having a surface coated with the substrate of the present disclosure. Exemplary cell culture article includes, but is not limited to, cell culturing dishes, cell culture plates such as single and multi-well plates, such as 6, 12, 96, 384, and 1536 well plates.

In another aspect, the present invention provides a cell culture system comprising the cell culture article of the present disclosure. In some embodiments, the cell culture system further comprises cells. In some embodiments, the cell culture system further comprises culture media.

In some embodiments, the cell culture system disclosed herein enables an efficient and scalable multiplication of cells, in particular, single cells or low-density cells (e.g., cells with an abundance of less than 1000 in one milliliter) into 3D, making it possible to form 3D cell culture on difficult cell types that did not form on current platforms in the market (e.g., Ultra Low Attachment (ULA) plate, Hanging-Drop).

As disclosed herein, one or more parameters of the polyelectrolyte multilayers and the culture medium may be selected by the user, based on one or more microenvironment selection criteria for the cells.

The cell culture system disclosed herein enables not only cell attachment and growth, but also the viable harvest of cultured cells (e.g. 3D cell culture, tissue and organs). The inability to harvest viable cells is a significant drawback in current platforms on the market, and it leads to difficulty in building and sustaining a sufficient number of cells for production capacity. According to an aspect of embodiments of this disclosure, it is possible to harvest viable cells from the cell culture system, including between 80% to 100% viable, or about 85% to about 99% viable, or about 90% to about 99% viable. For example, of the cells that are harvested, at least 80% are viable, at least 85% are viable, at least 90% are viable, at least 91% are viable, at least 92% are viable, at least 93% are viable, at least 94% are viable, at least 95% are viable, at least 96% are viable, at least 97% are viable, at least 98% are viable, or at least 99% are viable. In some embodiments, cells can be released from the cell culture surface with using a cell dissociation enzyme, for example, trypsin, TrypLE, or Accutase. In preferred embodiments, cells can be released from the cell culture surface without using a cell dissociation enzyme.

In another aspect, the present disclosure provides methods for culturing cells, and optionally harvesting cells using the substrate disclosed herein. The method for culturing cells comprises the steps of: (a) providing a substrate of the present disclosure; (b) seeding cells on the substrate; (c) culturing the cells under suitable condition; and (d) optionally harvesting the cultured cells. In some embodiments, the cultured cells (i.e. cell products) are 3D cell culture such as spheroids. In some embodiments, the spheroids generated herein are adhered to the substrate. In some embodiments, the spheroids generated herein are semi-attached to the substrate. In some embodiments, the spheroids are derived from single cells via single cell proliferation. In some embodiments, the substrate of the invention is housed in a cell culture article. Any suitable article can be employed in the methods of exemplary embodiments. The cultured cells (e.g., cultured and harvested cells) may be used for various applications such as analysis and characterization, screening drugs, isolating single-cell derived clone, generating cell banks, and generating animal models.

As described herein, the cells are living cells. In some embodiments, the cells are mammalian cells. In some embodiments, the cells are tissue cells, immune cells, endothelial cells, stem cells, epithelial cells, mesenchymal cells, mesothelial cells, tumor cells or tumor-associated cells.

As described herein, culturing the cells comprise maintaining and/or proliferating cells. In some embodiments, culturing the cells comprises maintaining cells. In some embodiments, culturing the cells comprises proliferating cells. In some embodiments, culturing the cells may further comprise differentiating cells.

In some embodiments, the cells are stem cells such as mesenchymal stem cells (MSCs) or pluripotent stem cells (PSCs) including embryonic stem cells (ESCs) and induced pluripotent stem cells (iPSCs).

In some embodiments, the cells are tumor cells, and the cultured cells are tumor spheroids. The tumor spheroids may be derived from a cell line, a tumor tissue or a liquid biopsy. In some embodiments, tumor spheroids described herein are derived from circulating tumor cells (CTCs) isolated from a blood sample obtained from a cancer patient. In some embodiments, the blood sample described herein is a whole blood. The blood sample can be obtained by liquid biopsy. In some embodiments, the cancer patient described herein is a human cancer patient having a metastatic cancer. In some embodiments, the blood sample is obtained from the cancer patient before, during, and/or after therapeutic treatment.

In some embodiments, the substrate of the invention can be used as a patch, for example, attached to the skin. The cultured cells generated herein may be used for cell therapy.

Another aspect of the present disclosure provides a method of preparing a single-cell derived spheroid in vitro, the method comprising the steps of: (a) providing a cell culture system comprising the substrate of the present disclosure; (b) isolating cells (e.g. tumor cells and/or tumor-associated cells) from a sample to provide isolated cells; (c) seeding the isolated cells on the substrate; and (d) culturing the cells under a suitable medium for a time sufficient to produce one or more spheroids, wherein the one or more spheroids are single-cell derived.

Another aspect of the present disclosure provides methods for isolating single cell derived clones, each composed of a homogenous cell population that is genetically identical.

DETAILED DESCRIPTION OF THE INVENTION

The present disclosure relates to a substrate useful for cell culture, in particular, 3D cell culture. The substrate comprises a surface coating that can induce the formation of highly uniform 3D cell culture, making it possible to form 3D cell culture on difficult primary cell types that did not form on any other low attachment surface. The substrate disclosed herein is configurable, flexible, and adaptable to any suitable cell culture articles in a variety of configurations.

Substrates of the Invention

Figure 1A:
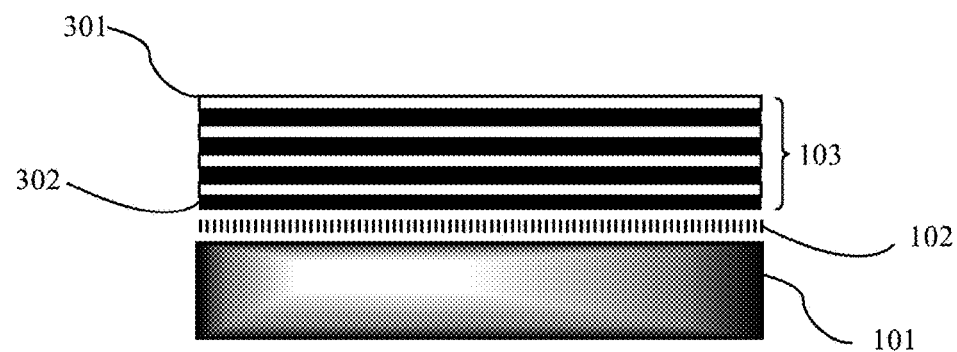
FIG. 1A is a side cross-sectional view of an embodiment of the substrate of the present disclosure. An absorbent polymer 102 is deposited on an elastomer 101 (e.g., PDMS). 101 and 102 are not crosslinked. 301 is a polyanion. 302 is a polycation. 103 is an embodiment of polyelectrolyte multiplayers including 4 bilayers of 301 and 302. The outermost layer is 301.
Figure 1B:
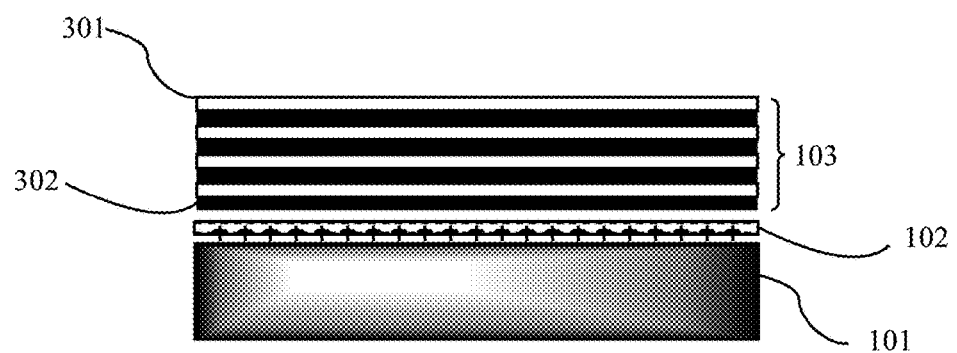
FIG. 1B is a side cross-sectional view of an embodiment of the substrate of the present disclosure. An absorbent polymer 102 is deposited on an elastomer 101 (e.g., PDMS). 101 and 102 are crosslinked. 301 is a polyanion. 302 is a polycation. 103 is an embodiment of polyelectrolyte multiplayers including 4 bilayers of 301 and 302. The outermost layer is 301.
Figure 2A:
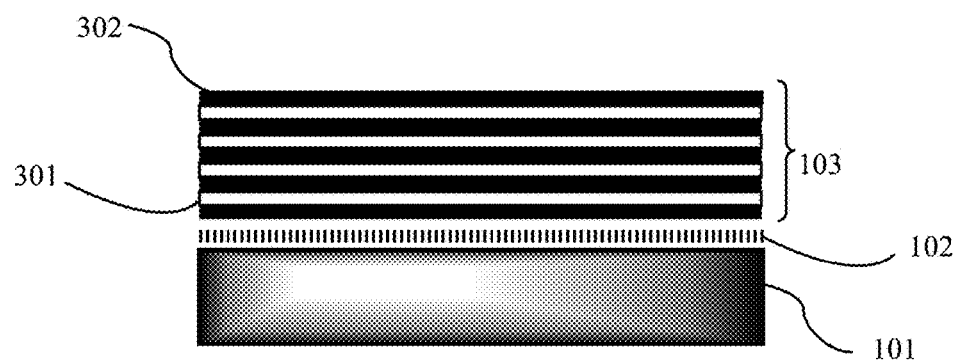
FIG. 2A is a side cross-sectional view of an embodiment of the substrate of the present disclosure. An absorbent polymer 102 is deposited on an elastomer 101 (e.g., PDMS). 101 and 102 are not crosslinked. 301 is a polyanion. 302 is a polycation. 103 is an embodiment of polyelectrolyte multiplayers including 5 layers of 302 and 4 layers of 301. The outermost layer is 302.
Figure 2B:
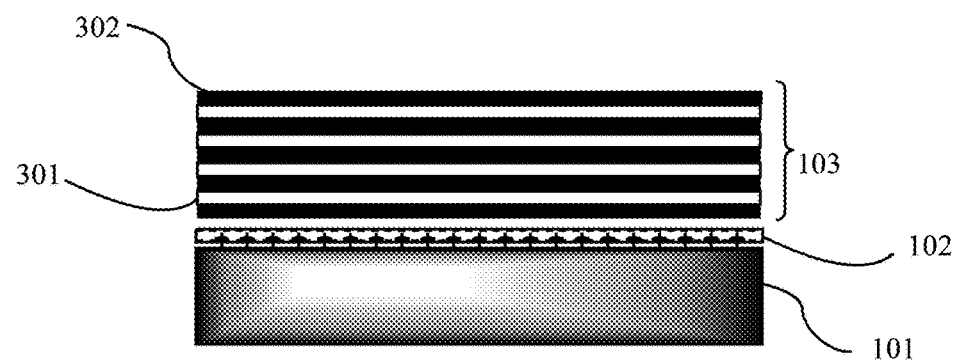
FIG. 2B is a side cross-sectional view of an embodiment of the substrate of the present disclosure. An absorbent polymer 102 is deposited on an elastomer 101 (e.g., PDMS). 101 and 102 are crosslinked. 301 is a polyanion. 302 is a polycation. 103 is an embodiment of polyelectrolyte multiplayers including 5 layers of 302 and 4 layers of 301. The outermost layer is 302.
Figure 3A:
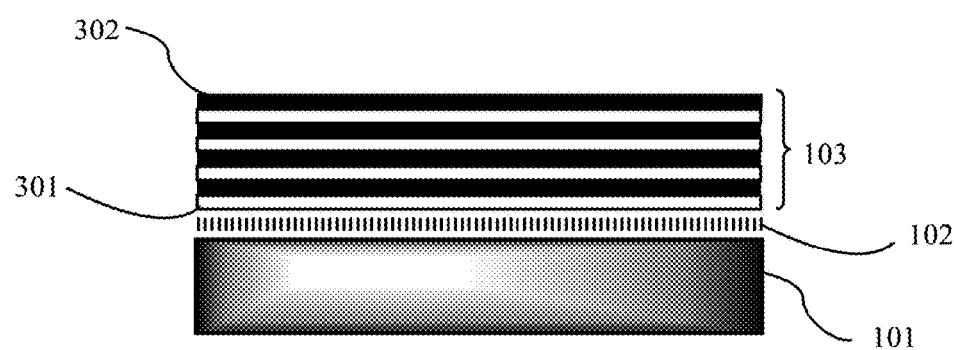
FIG. 3A is a side cross-sectional view of an embodiment of the substrate of the present disclosure. An absorbent polymer 102 is deposited on an elastomer 101 (e.g., PDMS). 101 and 102 are not crosslinked. 301 is a polyanion. 302 is a polycation. 103 is an embodiment of polyelectrolyte multiplayers including 4 bilayers of 301 and 302. The outermost layer is 302.
Figure 3B:
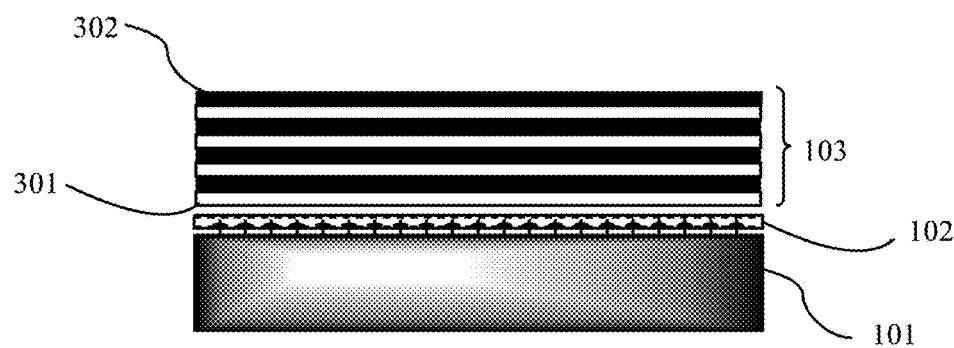
FIG. 3B is a side cross-sectional view of an embodiment of the substrate of the present disclosure. An absorbent polymer 102 is deposited on an elastomer 101 (e.g., PDMS). 101 and 102 are crosslinked. 301 is a polyanion. 302 is a polycation. 103 is an embodiment of polyelectrolyte multiplayers including 4 bilayers of 301 and 302. The outermost layer is 302.
Figure 4A:
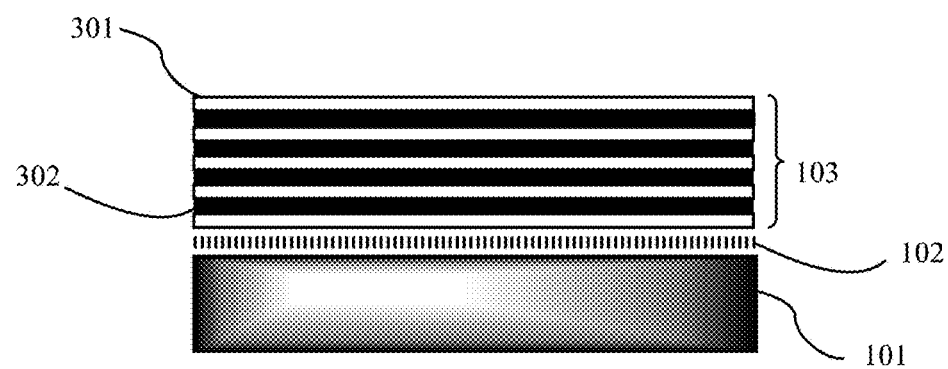
FIG. 4A is a side cross-sectional view of an embodiment of the substrate of the present disclosure. An absorbent polymer 102 is deposited on an elastomer 101 (e.g., PDMS). 101 and 102 are not crosslinked. 301 is a polyanion. 302 is a polycation. 103 is an embodiment of polyelectrolyte multiplayers including 5 layers of 301 and 4 layers of 302. The outermost layer is 301.
Figure 4B:
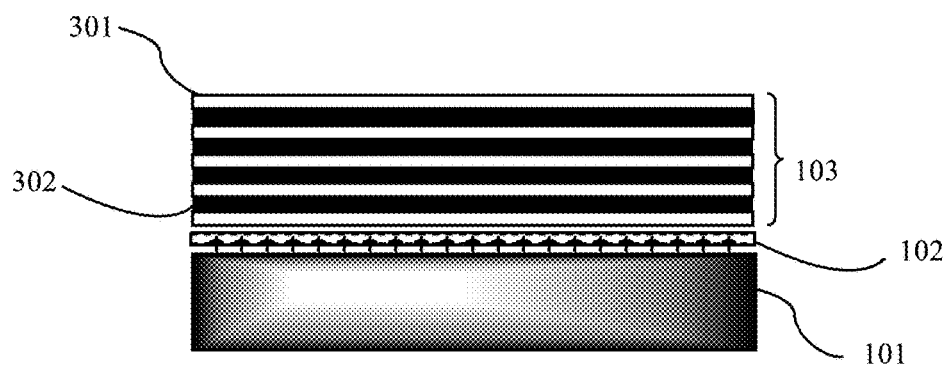
FIG. 4B is a side cross-sectional view of an embodiment of the substrate of the present disclosure. An absorbent polymer 102 is deposited on an elastomer 101 (e.g., PDMS). 101 and 102 are crosslinked. 301 is a polyanion. 302 is a polycation. 103 is an embodiment of polyelectrolyte multiplayers including 5 layers of 301 and 4 layers of 302. The outermost layer is 301.
Figure 5:
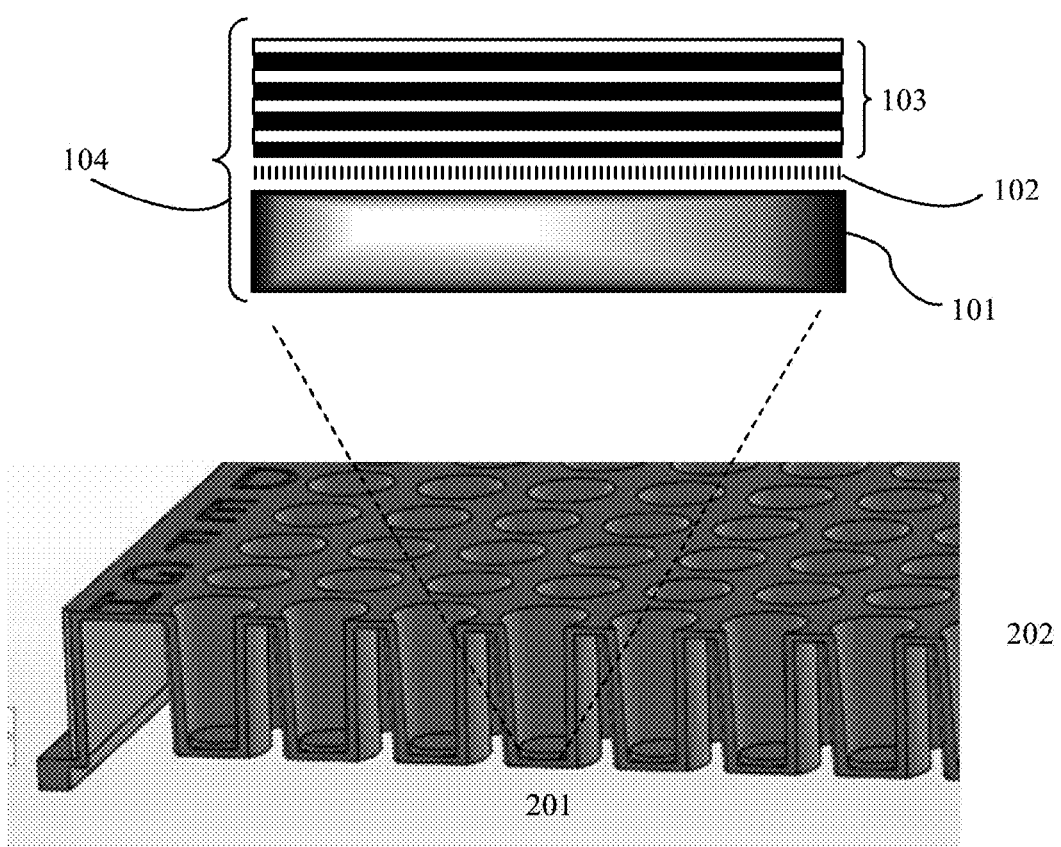
FIG. 5 shows an exemplary embodiment of the cell culture article 202. 201 is a well of the cell culture article for housing the substrate 104 comprising an elastomer (e.g., PDMS) 101, an absorbent polymer 102 and polyelectrolyte multiplayers 103. 104 can be inserted into 201 in the cell culture article 202. 202 can be regarded as 6, 12, 24, 96 and more well plate for cell culture.

The present disclosure provides a substrate for use in coating cell culture articles or culturing cells. The substrate disclosed herein comprises polyelectrolyte multilayers comprising one or more bilayers of polyelectrolytes, an absorbent polymer, and an elastomer membrane (e.g., PDMS). In some instances, the substrate is as illustrated in FIG. 1. As show in FIG. 1, 104 indicates an illustrative substrate of the invention deposited within the well 201 of a cell culturing plate 202. Polyelectrolyte multilayers 103 are deposited on top of the absorbent polymer 102. An elastomer membrane 101 is deposited directly on top of the well surface 201, whereas the absorbent polymer 102 is deposited on top of the elastomer membrane 101.

1) Elastomers

The substrate disclosed herein comprises an elastomer membrane as a support. In some embodiments, the elastomer described herein is a silicone elastomer. The silicone elastomer described herein may be hydrophilic or hydrophobic. In some embodiments, the silicone elastomer is a hydrophilic silicone elastomer. In some embodiments, the silicone elastomer is a hydrophobic silicone elastomer. In preferred embodiments, the silicone elastomer is polydimethylsiloxane (PDMS) (e.g., sold under the trade name Sylgard 184® from Dow Corning, Alpagel K from Alpine Technische Produkte GmbH, or Nusil Shore 00 from Silicone Solutions).

In some instances, the elastomer membrane further comprises one or more mineral fillers such as silica, alumina, calcium carbonate, or silicone resin. The elastomer membrane may further comprise one or more additives to enhance, e.g., color, rheology, and/or shelf life.

In some instances, the silicone elastomer membrane may have a thickness of less than 200 mm, less than 100 mm, less than 50 mm, less than 40 mm, less than 30 mm, less than 20 mm, less than 10 mm, or less than 1 mm. In some cases, the silicone elastomer membrane has a thickness of less than 100 mm. In some cases, the silicone elastomer membrane has a thickness of less than 50 mm. In some cases, the silicone elastomer membrane has a thickness of less than 10 mm. In some cases, the silicone elastomer membrane has a thickness of less than 1 mm.

2) Absorbent Polymers

Absorbent polymers described herein are hydrophilic polymers that are water soluble and may swell as a result of uptake and retention of aqueous solutions. A non-limiting list of absorbent polymers that may be used with the present invention includes hydrophilic and biocompatible grades of the following polymers and their derivatives: poly(vinyl alcohol) (PVA), ethylene vinyl alcohol co-polymers (typically non-biodegradable materials which degree of hydrophilicity depends on distribution of ethylene (hydrophobic) and vinyl alcohol (hydrophilic) groups), co-polymers of polyvinyl alcohol and ethylene vinyl alcohol, polyacrylate compositions, polyurethane compositions, poly(ethylene glycol) (PEG), otherwise known as poly(oxyethylene) (POE) and poly(ethylene oxide) (PEO), and its derivatives including but not limited to polyethylene glycol methacrylate (PEGMA), polyethylene glycol dimethacrylate (PEGDMA) and polyethylene glycol diacrylate (PEGDA); nitrogen-containing materials such as polyacrylamide (without acrylamide toxic residuals), polyvinylpyrrolidone, polyvinylamine, and polyethyleneimine; electrically charged materials such as poly(lactic acid) also known as polylactide in various forms (e.g. poly-L-lactide (PLLA) and its derivatives, poly-D-lactide (PDLA) and its derivatives, poly(L-lactide-co-D,L-lactide) (PLDLLA) and its derivatives), poly(glycolic acid) (PGA) also known as polyglycolide, co-polymers of lactic acid and glycolic acid poly(lactic-co-glycolic acid) (PL-co-GA), co-polymers of PLA and/or PGA with PEG; polymethacrylic acid; poly(hydroxyethyl methacrylate) (poly-HEMA), among other absorbent, hydrophilic and biocompatible materials known in the art.

In some embodiments, the absorbent polymer is selected from the group consisting of poly(vinyl alcohol) (PVA), copolymers of ethylene vinyl alcohol, copolymers of polyvinyl alcohol and ethylene vinyl alcohol, polyacrylate compositions, polyurethane compositions, poly(ethylene glycol) (PEG), PEG-acrylate, polyethylene glycol methacrylate (PEGMA), polyethylene glycol dimethacrylate (PEGDMA), polyethylene glycol diacrylate (PEGDA), polyacrylamide (PAM), polyvinylpyrrolidone (PVP), polyvinylamine (PVAm), polyethyleneimine (PEI), poly-L-lactide (PLLA), poly-D-lactide (PDLA), poly(L-lactide-co-D,L-lactide) (PLDLLA), poly(glycolic acid) (PGA), poly(lactic-co-glycolic acid) (PL-co-GA), poly(methyl methacrylate) (PMMA) and poly(hydroxyethyl methacrylate) (p-HEMA).

In some embodiments, the absorbent polymer is selected from the group consisting of PVA, PEG, PEG-acrylate, polylactide, PMMA, p-HEMA, a combination or a derivative thereof. In some embodiments, the absorbent polymer is PVA or a derivative thereof. In some embodiments, the absorbent polymer is PEG or PEG-acrylate such as PEGMA, PEGDMA or PEGDA. In some embodiments, the absorbent polymer is polylactide or a derivative such as PLLA, PDLA or PLDLLA. In some embodiments, the absorbent polymer is PGA or a derivative such as PLGA. In some embodiments, the absorbent polymer is PMAA or a derivative such as pHEMA.

In some embodiments, the absorbent polymer has an average molecular weight of from about 2,500 g/mol to about 200,000 g/mol. In some cases, the average molecular weight of the absorbent polymer is from about 5,000 g/mol to about 175,000 g/mol, from about 5,000 g/mol to about 150,000 g/mol, from about 5,000 g/mol to about 125,000 g/mol, from about 5,000 g/mol to about 100,000 g/mol, from about 5,000 g/mol to about 75,000 g/mol, from about 5,000 g/mol to about 50,000 g/mol, from about 5,000 g/mol to about 25,000 g/mol, from about 5,000 g/mol to about 10,000 g/mol, from about 10,000 g/mol to about 175,000 g/mol, from about 10,000 g/mol to about 150,000 g/mol, from about 10,000 g/mol to about 125,000 g/mol, from about 10,000 g/mol to about 100,000 g/mol, from about 10,000 g/mol to about 75,000 g/mol, from about 10,000 g/mol to about 50,000 g/mol, from about 10,000 g/mol to about 25,000 g/mol, from about 20,000 g/mol to about 150,000 g/mol, or from about 50,000 g/mol to about 150,000 g/mol.

In some embodiments, the absorbent polymer is PVA. PVA can have an average molecular weight ranging from about 10,000 g/mol to about 125,000 g/mol. In some instances, PVA has an average molecular weight of from about 10,000 g/mol to about 100,000 g/mol, from about 10,000 g/mol to about 75,000 g/mol, from about 10,000 g/mol to about 50,000 g/mol, from about 20,000 g/mol to about 125,000 g/mol, from about 20,000 g/mol to about 100,000 g/mol, from about 20,000 g/mol to about 75,000 g/mol, from about 20,000 g/mol to about 50,000 g/mol, from about 50,000 g/mol to about 125,000 g/mol, or from about 50,000 g/mol to about 100,000 g/mol.

In some embodiment, the absorbent polymer is PEG. In some instances, the average molecular weight of PEG is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some instances, the PEG utilized herein is a discrete PEG (dPEG). A discrete PEG can be a polymeric PEG comprising more than one repeating ethylene oxide units. In some cases, the discrete PEG comprises from 2 to 60, from 2 to 50, or from 2 to 48 repeating ethylene oxide units. In some cases, the dPEG comprises 2, 3, 4, 5, 6, 7, 8, 9, 10, 11, 12, 13, 14, 15, 16, 17, 18, 19, 20, 22, 24, 26, 28, 30, 35, 40, 42, 48, 50 or more repeating ethylene oxide units.

In certain embodiments, the volume of the absorbent polymer is from about 0.01% to about 10% of the total volume of the surface coating. In some instances, the absorbent polymer is from about 0.01% to about 9% v/v, from about 0.01% to about 8% v/v, from about 0.01% to about 7% v/v, from about 0.01% to about 6% v/v, from about 0.01% to about 5% v/v, from about 0.01% to about 4% v/v, from about 0.01% to about 3% v/v, from about 0.01% to about 2% v/v, from about 0.01% to about 1% v/v, from about 0.1% to about 10% v/v, from about 0.1% to about 9% v/v, from about 0.1% to about 8% v/v, from about 0.1% to about 7% v/v, from about 0.1% to about 6% v/v, from about 0.1% to about 5% v/v, from about 0.1% to about 4% v/v, from about 0.1% to about 3% v/v, from about 1% to about 10% v/v, from about 1% to about 9% v/v, from about 1% to about 8% v/v, from about 1% to about 7% v/v, from about 1% to about 6% v/v, from about 1% to about 5% v/v, from about 1% to about 4% v/v, from about 2% to about 10% v/v, or from about 5% to about 10% v/v, of the total volume of the surface coating. In some cases, the volume of the absorbent polymer (e.g. PVA or PEG) is about 0.01%, about 0.05%, about 0.1%, about 0.5%, about 1%, about 2%, about 3%, about 4%, about 5%, about 6%, about 7%, about 8%, about 9%, or about 10% of the total volume of the surface coating.

In some instances, the weight of the absorbent polymer (e.g. PVA or PEG) per total weight of the surface coating is from about 1% to about 50%. In some instances, the weight of the absorbent polymer per total weight of the surface coating is from about 1% to about 40%. In some instances, the weight of the absorbent polymer per total weight of the surface coating is from about 1% to about 30%. In some instances, the weight of the absorbent polymer per total weight of the surface coating is from about 1% to about 20%. In some instances, the weight of the absorbent polymer per total weight of the surface coating is from about 1% to about 10%.

3) Polyelectrolyte Multilayers

As disclosed herein, the substrate comprises polyelectrolyte multilayers (PEMs). PEMs described herein comprise a plurality of alternating layers of oppositely charged polymers (i.e., polyelectrolytes). The oppositely charged polymers described herein comprise a combination of a positively charged polyelectrolyte (also referred to herein as a polycation) and a negatively charged polyelectrolyte (also referred to herein as a polyanion).

Exemplary polycations include, but are not limited to, poly(L-lysine) (PLL), poly(L-arginine) (PLA), poly(L-ornithine) (PLO), poly(L-histidine) (PLH), polyethyleneimine (PEI), poly[$\alpha$-(4-aminobutyl)-L-glycolic acid] (PAGA), 2-(dimethylamino)ethyl methacrylate (DMAEMA), N,N-Diethylaminoethyl methacrylate (DEAEMA), and a combination thereof. In some instances, the polycation is PLL. In some instances, the polycation is PLO. In some instances, the polycation is PLH. In some instances, the polycation is PLA.

Exemplary polyanions include, but are not limited to, poly-L-glutamic acid (PLGA), poly-L-aspartic acid (PLAA), poly(acrylic acid), poly(methacrylic acid) (PMAA), poly(styrenesulfonic acid) (PSS), poly(N-isopropylacrylamide) (NIPAM), poly(2-acrylamido-2-methyl-1-propane sulfonic acid) (PAMPS), and a combination thereof. In some instances, the polyanionis PLGA. In some instances, the polyanion is PLAA.

Polyelectrolyte multilayers may be formed by depositing polycations and polyanions in an alternative fashion via layer-by-layer assembly. Polyelectrolyte multilayers described herein include at least one bilayer including a polycation layer and a polyanion layer.

In some embodiments, the PEMs may include from about 1 bilayers to about 100 bilayers. In some embodiments, the PEMs may include from about 1 bilayers about 50 bilayers. In some embodiments, the PEMs may include from about 1 bilayers to about 30 bilayers. In some embodiments, the PEMs may include from about 1 bilayers to about 20 bilayers. In some embodiments, the number of bilayers is 1, 2, 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16. In some embodiments, the number of bilayers is 3. In some embodiments, the number of bilayers is 4. In some embodiments, the number of bilayers is 5. In some embodiments, the number of bilayers is 6. In some embodiments, the number of bilayers is 7. In some embodiments, the number of bilayers is 8. In some embodiments, the number of bilayers is 9. In some embodiments, the number of bilayers is 10. In some embodiments, the number of bilayers is 11. In some embodiments, the number of bilayers is 12. In some embodiments, the number of bilayers is 13. In some embodiments, the number of bilayers is 14. In some embodiments, the number of bilayers is 15. In some embodiments, the number of bilayers is 16. In some embodiments, the number of bilayers is 17. In some embodiments, the number of bilayers is 18. In some embodiments, the number of bilayers is 19. In some embodiments, the number of bilayers is 20.

In some embodiments, the polyelectrolyte multilayers described herein comprise one or more bilayers of positively charged polyelectrolyte(s) and negatively charged polyelectrolyte(s), in which the polycation is selected from PLL, PLO PLH, and PLA, and the polyanion is selected from PLGA and PLAA. In some embodiments, the number of sets ranges from 1 to 100, 3 to 60, from 3 to 50, or from 3 to 30. In some embodiments, the number of sets is greater than 3, 4, 5, 6, 7, 8, 9, 10, 11, 12, 13, 14, 15, 16, 17, 18, 19 or 20. In some embodiments, the number of sets is 3, 4, 5, 6, 7, 8, 9, 10, 11, 12, 13, 14, 15, 16, 17, 18, 19 or 20. In some embodiments, the number of sets is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLL and PLGA. In some embodiments, the number of bilayers of PLL and PLGA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLO and PLGA. In some embodiments, the number of bilayers of PLO and PLGA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLH and PLGA. In some embodiments, the number of bilayers of PLH and PLGA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLA and PLGA. In some embodiments, the number of bilayers of PLA and PLGA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLL and PLAA. In some embodiments, the number of bilayers of PLL and PLAA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLO and PLAA. In some embodiments, the number of bilayers of PLO and PLAA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLH and PLAA. In some embodiments, the number of bilayers of PLH and PLAA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

In some embodiments, the polyelectrolyte multilayers described herein comprise one or more bilayers of PLA and PLAA. In some embodiments, the number of bilayers of PLA and PLAA ranges from 1 to 100, 3 to 60, from 3 to 50, or from 3 to 30. In some embodiments, the number of bilayers is greater than 3, 4, 5, 6, 7, 8, 9, 10, 11, 12, 13, 14, 15, 16, 17, 18, 19 or 20. In some embodiments, the number of bilayers is 3, 4, 5, 6, 7, 8, 9, 10, 11, 12, 13, 14, 15, 16, 17, 18, 19 or 20. In some embodiments, the number of bilayers is in a range of 1-10, 1-8, 1-5, 3-20, 5-20, 10-20, 11-19, 12-18, 13-17, or 14-16.

The thickness of the PEM as a thin film may be in a broad range, for example, in a range from about 30 nm to about 30 μm, or from about 100 nm to about 20 μm. In some embodiments, the thickness is about 100 nm to about 500 nm, about 500 nm to about 1 μm, or about 1 μm to about 10 μm. In some embodiments, the thickness is about 200, 400, 600, 800 nm, or any number in between. In some embodiments, the thickness is about 1, 5, 10, 15 or 20 μm, or any number in between.

A number of methodologies are available for characterizing PEMs. In some embodiments, the methodologies may comprise ellipsometry (thickness), quartz crystal microbalance with dissipation monitoring (mass adsorbed, viscoelasticity), contact angle analysis (surface energy), Fourier transform infrared spectroscopy (functional groups), X-ray photoelectron spectroscopy (chemical composition), scanning electron microscopy (surface structure), and atomic force microscopy (roughness/surface structure).

In some embodiments, PEMs may be deposited by pipetting polyanion or polycation solutions into/onto the dish, either as a mixture or sequentially.

In some embodiments, a PEM is formed on the surface by dip coating. In dip coating, the substrate is immersed in a polyelectrolyte solution for a set amount of time (usually 10-15 min), followed by multiple rinses and immersion in a second polyelectrolyte solution of opposite charge. This process is repeated until the desired number of layers is achieved.

In some embodiments, the PEM is formed on the surface by spray coating. In some embodiments, a polyelectrolyte may be sprayed onto the surface for 3-10 sec followed by a rest/draining period of 10-30 sec, washing of the surface with a water spray for 3-20 sec, an additional rest period of 10 sec, and repeating the cycle with a polyelectrolyte of opposite charge.

In some embodiments, the PEM is formed on the surface by spin coating. Spin coating is a highly controlled method for solution-based coating of a system. A typical spin coating procedure includes spin coating for 10-15 sec, rinsing at least once by "spin coating" water for 15-30 sec and repeating the procedure with the oppositely charged polyelectrolyte. The wash step may not be necessary in spin coating.

4) Construction of Cell Culture Substrate

Another aspect of the present disclosure features a method for manufacturing the cell culture substrate of the present disclosure. The method described herein comprises the steps of: (a) providing a support; (b) applying an elastomer onto a surface of the support; (c) applying an absorbent polymer onto the elastomer; (d) sequentially depositing on the absorbent polymer alternating layers of polyelectrolytes to form a multilayered membrane; and (e) delaminating the multilayered membrane from the support to obtain a substrate.

In some embodiments, the elastomer described herein is a silicon elastomer. In some embodiments, the silicon elastomer is polydimethylsiloxane (PDMS). In some embodiments, the PDMS comprises a hydrophilic surface. In some embodiments, the PDMS comprises a hydrophobic surface. In some embodiments, a surface modification is employed to convert the PDMS hydrophobic surface to a hydrophilic surface.

In some embodiments, the method of preparing the substrate of the present disclosure comprises the steps of: (a) providing a PDMS having a hydrophobic surface; (b) modifying the hydrophobic surface of PDMS with a treatment; (c) applying an absorbent polymer to the modified surface of PDMS; and (d) sequentially depositing on the absorbent polymer alternating layers of polyelectrolytes, thereby a substrate comprising a multilayered membrane is obtained.

In some embodiments, the treatment comprises a plasma treatment, corona discharge or UV ozone treatment. In some embodiments, the hydrophobic surface of PDMS is irradiated after the treatment. In some embodiments, the PDMS surface is hydrophilized after applying the absorbent polymer to the modified surface of PDMS. In some embodiments, the hydrophobic surface of PDMS can be converted to a hydrophilic surface after applying PVA to the modified surface of PDMS. In some embodiments, the hydrophobic surface of PDMS is modified by hydrosilylation. In some embodiments, the PDMS surface is hydrophilized after applying a PEG-acrylate to the surface-modified PDMS. In some embodiments, the PDMS and PEG are crosslinked to provide a hydrophilized PDMS surface. A cross-linking agent may be used to facilitate the crosslink between the absorbent polymer and PDMS. Exemplary cross-linking agents include, but are not limited to, maleic acid, formaldehyde, glutaraldehyde, butanal (butyraldehyde), sodium borate, and a combination thereof.

As described herein, a surface is hydrophilic if a contact angle for a water droplet on the surface is less than 90 degrees (the contact angle is defined as the angle passing through the drop interior). Embodiments include hydrophilic surfaces with a contact angle from 90 to 0 degrees; Artisans will immediately appreciate that all ranges and values between the explicitly stated bounds are contemplated, with, e.g., any of the following being available as an upper or lower limit: 90, 80, 70, 60, 50, 40, 30, 20, 10, 5, 2, 0 degrees.

In some embodiments, the substrate described herein comprises (polyanion/polycation)$_n$/X/PDMS, wherein the polyanion/polycation is selected from PLGA/PLL, PLAA/PLL, PLGA/PLA, PLAA/PLA, PLGA/PLO, PLAA/PLO, PLGA/PLH and PLAA/PLH, X is PVA, PEG, PEG-acrylate or PVP, and n is an integer number ranging from 1 to 20, optionally 1, 2, 3, 4, 5, 6, 7, 8, 9, 10, 11, 12, 13, 14, 15, 16, 17, 18, 19, 20. In some embodiments, n is in a range of 1-10, 1-8, 1-5, 3-20, 5-20, 10-20, 11-19, 12-18, 13-17, or 14-16. In some embodiments, X is PEG-acrylate, and PEG-acrylate is crosslinked to PDMS. In some embodiments, X is PVA, and PDMS and PVA are free of crosslinks.

In some embodiments, the substrate described herein comprises (polycation/polyanion)$_n$/X/PDMS, wherein the polycation/polyanion is selected from PLL/PLGA, PLL/PLAA, PLA/PLGA, PLA/PLAA, PLO/PLGA, PLO/PLAA, PLH/PLGA and PLH/PLAA, X is PVA, PEG, PEG-acrylate or PVP, and n is an integer number ranging from 1 to 20, optionally 1, 2, 3, 4, 5, 6, 7, 8, 9, 10, 11, 12, 13, 14, 15, 16, 17, 18, 19, 20. In some embodiments, n is in a range of 1-10, 1-8, 1-5, 3-20, 5-20, 10-20, 11-19, 12-18, 13-17, or 14-16. In some embodiments, X is PEG-acrylate, and PEG-acrylate is crosslinked to PDMS. In some embodiments, X is PVA, and PDMS and PVA are free of crosslinks.

In some embodiments, the substrate described herein polycation (polyanion/polycation)$_n$/X/PDMS, wherein the polyanion/polycation is selected from PLGA/PLL, PLAA/PLL, PLGA/PLA, PLAA/PLA, PLGA/PLO, PLAA/PLO, PLGA/PLH and PLAA/PLH, X is PVA, PEG, PEG-acrylate or PVP, and n is an integer number ranging from 1 to 20, optionally 1, 2, 3, 4, 5, 6, 7, 8, 9, 10, 11, 12, 13, 14, 15, 16, 17, 18, 19, 20. In some embodiments, n is in a range of 1-10, 1-8, 1-5, 3-20, 5-20, 10-20, 11-19, 12-18, 13-17, or 14-16. In some embodiments, X is PEG-acrylate, and PEG-acrylate is crosslinked to PDMS. In some embodiments, X is PVA, and PDMS and PVA are free of crosslinks.

In some embodiments, the substrate described herein polyanion (polycation/polyanion)$_n$/X/PDMS, wherein the polycation/polyanion is selected from PLL/PLGA, PLL/PLAA, PLA/PLGA, PLA/PLAA, PLO/PLGA, PLO/PLAA, PLH/PLGA and PLH/PLAA, X is PVA, PEG, PEG-acrylate or PVP, and n is an integer number ranging from 1 to 20, optionally 1, 2, 3, 4, 5, 6, 7, 8, 9, 10, 11, 12, 13, 14, 15, 16, 17, 18, 19, 20. In some embodiments, n is in a range of 1-10, 1-8, 1-5, 3-20, 5-20, 10-20, 11-19, 12-18, 13-17, or 14-16. In some embodiments, X is PEG-acrylate, and PEG-acrylate is crosslinked to PDMS. In some embodiments, X is PVA, and PDMS and PVA are free of crosslinks.

The surface coating of the elastomer membrane described herein can be dehydrated or hydrated. In some embodiments, the surface coating is in a dehydrated state. In other embodiments, the surface coating is in a hydrated state. As used herein, a "dehydrated state" and a "hydrated state" each refers to a volume of an aqueous solution (e.g., water) in reference to the total volume of the surface coating. In the dehydrated state, the volume of the aqueous solution (e.g., water) is less than 20%, less than 15%, less than 10%, less than 5%, less than 1%, or less than 0.5% of the total volume of the surface coating. In a hydrated state, the volume of the aqueous solution (e.g., water) is at least 20%, at least 30%, at least 40%, at least 50%, at least 60%, or higher of the total volume of the surface coating.

In some embodiments, the surface coating of the elastomer membrane described herein comprises an aqueous solution (e.g., water). In some cases, the aqueous solution (e.g., water) is from about 1% to about 60% by weight of the total weight of the surface coating. In some cases, the aqueous solution (e.g., water) is from about 1% to about 50% by weight, from about 1% to about 40% by weight, from about 1% to about 30% by weight, from about 1% to about 20% by weight, from about 10% to about 60% by weight, from about 10% to about 50% by weight, from about 10% to about 40% by weight, from about 10% to about 30% by weight, from about 10% to about 20% by weight, from about 20% to about 60% by weight, from about 20% to about 50% by weight, from about 20% to about 40% by weight, or from about 30% to about 60% by weight of the total weight of the surface coating.

In some embodiments, the substrate further comprises a filler. In some instances, the filler comprises a mineral filler such as but not limited to silica, alumina, calcium carbonate, or silicone resin.

Each of polycations and polyanions, and absorbent polymer may be dissolved in an aqueous solution for use in the present disclosure. The aqueous solution is free, or substantially free, of organic solvents. It will be understood that some minor amounts of organic solvents may be present in the aqueous solution, for example as a result some organic solvent remaining in the polymer after polymerization. As used herein, "substantially free," as it relates to an organic solvent in an aqueous solution, means that the aqueous solution comprises less than 1% of the organic solvent by weight. In many embodiments, the aqueous solution contains less than 0.8%, less than 0.5%, less than 0.2% or less that 0.1% of an organic solvent.

Each of polycations and polyanions, and absorbent polymer may be dissolved in an aqueous solution at any suitable concentration for the purposes of coating.

Cell Culture Systems

The present disclosure provides a cell culture system including a cell culture article comprising the substrate of the present disclosure, and configured to culture cells.

The substrate disclosed herein is configurable and adaptable to any suitable cell culture articles in a variety of configurations. Exemplary cell culture article includes, but is not limited to, cell culturing dishes, cell culture plates such as single and multi-well plates, such as 6, 12, 96, 384, and 1536 well plates. The cell culture article described herein may be made of any suitable material including glass materials such as soda-lime glass, pyrex glass, vycor glass, quartz glass; silicon; plastics or polymers such as polyethylene, polypropylene, polymethylpentene, cyclic olefin polymer, cyclic olefin copolymer, polyvinyl chloride, polyurethane, polyester, polyamide, ethylene-vinyl acetate copolymer, ethylene-vinyl alcohol copolymer, ethylene-acrylic acid copolymer, ethylene-methyl acrylate copolymer, ethylene-methacrylic acid copolymer, ethylene-methyl methacrylate copolymer, polyacrylic acid, polymethacrylic acid, methyl polyacrylate, and methyl polymethacrylate, or derivatives of these or the like.

In some embodiments, the cell culture system further comprises cells. In some embodiments, the cells are derived from cell lines. In some embodiments, the cells are mammalian cells. In some embodiments, the cells are human cells. In some embodiments, the cells are tissue cells, immune cells, endothelial cells, stem cells, epithelial cells, mesenchymal cells, mesothelial cells, cancer cells or tumor-associated cells. In some embodiments, the cell culture system further comprises a culture media.

The cell culture systems disclosed herein enable not only cell attachment and growth, but also the viable harvest of cultured cells (e.g. 3D cell culture, tissue and organs). According to some embodiments of the present disclosure, the cell culture systems can be used to harvest viable cells, including between 80% to 100% viable, or about 85% to about 99% viable, or about 90% to about 99% viable. For example, of the cells that are harvested, at least 80% are viable, at least 85% are viable, at least 90% are viable, at least 91% are viable, at least 92% are viable, at least 93% are viable, at least 94% are viable, at least 95% are viable, at least 96% are viable, at least 97% are viable, at least 98% are viable, or at least 99% are viable. In some embodiments, cells can be released from the cell culture systems with or without using a cell dissociation enzyme, for example, trypsin, TryPLE, or Accutase.

Methods and Uses Thereof

1) Methods for Culturing Cells

Without being bound to any particular theory, it is believed that the substrate disclosed herein enables robust multiplication and/or stable maintenance of cells. The present disclosure thus provides a method for culturing cells. The method comprises the steps of: (a) providing a cell culture system comprising the substrate of the present disclosure; (b) seeding cells on a surface of the substrate; and (c) culturing the cells under a suitable medium. In some embodiments, the cells are cultured for a sufficient period of time to form spheroids. In preferred embodiments, the spheroids are 3D spheroids. In some embodiments, the spheroids described herein are generated via single cell proliferation. In some embodiments, the spheroids described herein are generated via single cell proliferation without cell agglomeration. In some embodiments, the spheroids have uniform size.

In some embodiments, the cells described herein may be derived from a cell line, a tissue biopsy or a liquid biopsy. In some embodiments, the cells are mammalian cells. In some embodiments, the cells are human cells. In some embodiments, the cells are tissue cells, immune cells, endothelial cells, stem cells, epithelial cells, mesenchymal cells, mesothelial cells, cancer cells or tumor-associated cells.

In some embodiments, the cells described herein are stem cells such as mesenchymal stem cells (MSCs) or pluripotent stem cells (PSCs) including embryonic stem cells (ESCs) and induced pluripotent stem cells (iPSCs).

In some embodiments, the cells described herein are cancer cells. Exemplary cancer described herein includes, but is not limited to, acute lymphatic cancer, acute myeloid leukemia, alveolar rhabdomyosarcoma, bone cancer, brain cancer, breast cancer, cancer of the anus, anal canal or anorectum cancer, cancer of the eye, cancer of the intrahepatic bile duct cancer, cancer of the joints, cancer of the neck, gallbladder or pleura cancer, cancer of the nose, nasal cavity or middle ear, cancer of the oral cavity, cancer of the vulva, chronic lymphatic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum cancer, omentum and mesentary cancer, pharynx cancer, prostate cancer, rectal cancer, renal cancer, skin cancer, small intestine cancer, soft tissue cancer, stomach cancer, testicular cancer, thyroid cancer, ureter cancer, and urinary bladder cancer.

In some embodiments, the cells described herein are tumor-associated cells. Exemplary tumor-associated cells include, but are not limited to, tumor cell clusters, tumor infiltrating lymphocytes (TILs), cancer associated macrophage-like cells (CAMLs), tumor-associated macrophages (TAMs), tumor-associated monocyte/macrophage lineage cells (MMLCs), cancer stem cells, tumor microemboli, tumor-associated stromal cells (TASC), tumor-associated myeloid cells (TAMCs), tumor-associated regulatory T cells (Treg), cancer-associated fibroblasts (CAFs), tumor-derived endothelial cells (TECs), tumor-associated neutrophils (TAN), tumor-associated platelets (TAP), tumor-associated immune cells (TAI), myeloid-derived suppressor cells (MDSC), and a combination thereof.

Exemplary cells include low-density cells, single cells, rare cells, or a combination thereof. Low-density cells can be cells when seeded, are less than 5000 per cm$^2$ on the substrate, e.g., no more than about any of 1, 5, 10, 20, 50, 100, 200, 300, 500, 1000, 2000, 3000, 4000, or 4500 per cm$^2$ on the substrate.

In some embodiments, seeding the isolated cells in step (c) comprises plating the cells at a density of between one cell and 10 cells per cm$^2$ on the substrate surface (i.e. cell growth surface). In some embodiments, seeding the isolated cells in step (c) comprises plating the cells at a density of between 10 cells and 100 cells per cm$^2$ on the substrate surface. In some embodiments, seeding the isolated cells in step (c) comprises plating the cells at a density of between 100 cells and 1000 cells per cm$^2$ on the substrate surface.

In some embodiments, the cells are cultured for a period of time ranging from about 2 days to about 5 weeks, such as from about 3 to about 14 days, for example about 7 days. In some embodiments, the cells are cultured for 3 days and the spheroids have an average diameter ranging from about 40 μm to about 200 μm.

Any suitable culture medium can be employed in the methods of exemplary embodiments. Exemplary culture medium includes, but is not limited to, Dulbecco's modified Eagle's medium (DMEM), epidermal growth factor (EGF) and/or basic fibroblast growth factor (bFGF), a mixture of Dulbecco's modified Eagle's medium (DMEM), supplemented with B27 supplement, epidermal growth factor (EGF) and basic fibroblast growth factor (bFGF).

2) Method of Preparing Single-Cell-Derived Spheroids

In another aspect, the present disclosure provides a provides a method of preparing a single-cell derived spheroid, the method comprising the steps of: (a) providing a cell culture system comprising the substrate of the present disclosure; (b) seeding cells on a surface of the substrate; and (d) culturing the cells under a suitable medium for a sufficient period of time to form spheroids, in which the spheroids are single-cell derived. The spheroids described herein are generated via single cell proliferation. In some embodiments, the spheroids have uniform size. In some embodiments, the single-cell-derived clones are semi-attached or loosely attached on the substrate of the present disclosure.

In some embodiments, the cells are derived from cell lines. In some embodiments, the cells are mammalian cells. In some embodiments, the cells are human cells. In some embodiments, the cells are tissue cells, immune cells, endothelial cells, stem cells, epithelial cells, mesenchymal cells, mesothelial cells, cancer cells or tumor-associated cells.

In some embodiments, the cells are stem cells such as mesenchymal stem cells (MSCs) or pluripotent stem cells (PSCs) including embryonic stem cells (ESCs) and induced pluripotent stem cells (iPSCs).

In some embodiments, the cells are cancer cells. In some embodiments, the cells are cancer cells. In certain embodiments, the cancer cells are isolated from human primary tumor tissue. In certain embodiments, the cancer cells are isolated from a blood sample of a cancer patient. Exemplary cancer described herein includes, but is not limited to, acute lymphatic cancer, acute myeloid leukemia, alveolar rhabdomycosarcoma, bone cancer, brain cancer, breast cancer, cancer of the anus, anal canal or anorectum cancer, cancer of the eye, cancer of the intrahepatic bile duct cancer, cancer of the joints, cancer of the neck, gallbladder or pleura cancer, cancer of the nose, nasal cavity or middle ear, cancer of the oral cavity, cancer of the vulva, chronic lymphatic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum cancer, omentum and mesentary cancer, pharynx cancer, prostate cancer, rectal cancer, renal cancer, skin cancer, small intestine cancer, soft tissue cancer, stomach cancer, testicular cancer, thyroid cancer, ureter cancer, and urinary bladder cancer.

In some embodiments, the cells are tumor-associated cells. Exemplary tumor-associated cells include, but are not limited to, tumor cell clusters, tumor infiltrating lymphocytes (TILs), cancer associated macrophage-like cells (CAMLs), tumor-associated macrophages (TAMs), tumor-associated monocyte/macrophage lineage cells (MMLCs), cancer stem cells, tumor microemboli, tumor-associated stromal cells (TASC), tumor-associated myeloid cells (TAMCs), tumor-associated regulatory T cells (Treg), cancer-associated fibroblasts (CAFs), tumor-derived endothelial cells (TECs), tumor-associated neutrophils (TAN), tumor-associated platelets (TAP), tumor-associated immune cells (TAI), myeloid-derived suppressor cells (MDSC), and a combination thereof.

Exemplary cells include low-density cells, single cells, rare cells, or a combination thereof. Low-density cells can be cells when seeded, are less than 5000 per cm$^2$ on the substrate, e.g., no more than about any of 1, 5, 10, 20, 50, 100, 200, 300, 500, 1000, 2000, 3000, 4000, or 4500 per cm$^2$ on the substrate.

In some embodiments, seeding the isolated cells in step (c) comprises plating the cells at a density of between one cell and 10 cells per cm$^2$ on the substrate surface (i.e. cell growth surface). In some embodiments, seeding the isolated cells in step (c) comprises plating the cells at a density of between 10 cells and 100 cells per cm$^2$ on the substrate surface. In some embodiments, seeding the isolated cells in step (c) comprises plating the cells at a density of between 100 cells and 1000 cells per cm$^2$ on the substrate surface.

In some embodiments, the culturing step occurs over a period of 2-8 days (e.g., 2, 3, 4, 5, 6, 7, or 8 days). In other embodiments, the culturing step culturing step occurs over a period of 7-14 days (e.g., 7, 8, 9, 10, 11, 12, 13, or 14 days). In other embodiments, the culturing step culturing step occurs over a period of 1-4 weeks (e.g., 1, 2, 3, or 4 weeks).

In some embodiments, the cells are cultured for 3 days and the spheroids have an average diameter ranging from about 40 µm to about 200 µm.

Any suitable culture medium can be employed in the methods of exemplary embodiments. Exemplary culture medium includes, but is not limited to, Dulbecco's modified Eagle's medium (DMEM), epidermal growth factor (EGF) and/or basic fibroblast growth factor (bFGF), a mixture of Dulbecco's modified Eagle's medium (DMEM), supplemented with B27 supplement, epidermal growth factor (EGF) and basic fibroblast growth factor (bFGF).

In some embodiments, the size of a single-cell derived spheroid less than 200 µm in diameter. In some embodiments, the size of a single-cell derived spheroid less than 150 µm in diameter. In some embodiments, the size of a single-cell derived spheroid is about 40, 50, 60, 70, 80, 90, 100, 110, 120, 130 or 140 µm in diameter.

In certain embodiments, the single-cell derived spheroid may be used for screening a therapeutic agent. In certain embodiments, a method of screening a therapeutic agent comprises: (a) applying a test substance to the single-cell derived spheroid generated thereof; and (b) evaluating an effect of the test substance on the single-cell derived spheroid. In some embodiments, the effect of the test substance is analyzed with an imaging system, e.g., to analyze the biochemical activity and/or the expression levels of a gene or a protein.

In some embodiments, the single-cell derived spheroid generated thereof is a tumor spheroid. In some embodiments, the test substance described herein is a chemotherapeutic drug, such as a cytotoxic or cytostatic chemotherapeutic drug. In some embodiments, the therapeutic agent is an immune checkpoint inhibitor, such as an immune checkpoint inhibitor. In some embodiments, the therapeutic agent is a nucleic acid drug. In some embodiments, the therapeutic agent is a therapeutic cell composition, including, but not limited to, T cells, natural killer (NK) cells, and dendritic cells.

In some embodiments, the cells are cultured for a period of time ranging from about 2 days to about 5 weeks, such as from about 3 to about 14 days, for example about 7 days. In some embodiments, the cells are cultured for 3 days and the at least one 3D spheroid has an average diameter ranging from about 40 µm to about 200 µm.

In some aspects, provided herein is a single-cell-derived spheroid (e.g., tumor spheroid) generated according to any one of the culture methods employing the cell culture systems described herein. In some aspects, there is provided a library of single-cell-derived spheroids (e.g., tumor spheroids) derived according to any one of the culture methods employing the cell culture systems described herein.

3) Method of Isolating Single-Cell-Derived Clones

Single-cell-derived clone has gained increasing importance as genome editing techniques have entered routine laboratory practice. Limiting dilution, the traditional method for isolating single cells, relies on statistical probabilities for monoclonality that can vary significantly with slight changes to protocols. The technique, while highly inefficient at isolating single cells, preserves cell viability. Conversely, flow cytometry can provide single cell clones with high efficiency but negatively affects cell viability. A common trait of these platforms is that they generally start with a suspension containing a large number of cells that are 'individualized' by random confinement in microstructures. Both of these methods are impractical when the cell population is small as they generate considerable cell loss during mixing and/or transfer. The method of the invention provides an efficient alternative for isolating viable single cell clones. In some embodiments, the method does not require individual confinement of cells in microstructures.

In some embodiments, there is provided herein a method of isolating a single-cell-derived clone. The method described herein comprises: 1) culturing a heterogeneous population of cells using a cell culture system comprising the substrate of the present disclosure to obtain a plurality of cell clones comprising a single-cell-derived clone; and 2) isolating the single-cell-derived clone from the cell culture system.

In some embodiments, the heterogeneous population of cells comprises adherent cells. In some embodiments, the heterogeneous population of cells comprises non-adherent cells. In some embodiments, the heterogeneous population of cells comprises cells isolated from a cell line. In some embodiments, the heterogeneous population of cells comprises cells isolated from a liquid biopsy of a subject. In some embodiments, the heterogeneous population of cells comprises cells isolated from a tissue biopsy of a subject. In some embodiments, the heterogeneous population of cells comprises cells that have been genetically engineered. In some embodiments, the heterogeneous population of cells comprises cells that have been engineered to comprise a genetic mutation. In some embodiments, the heterogeneous population of cells comprises cells that have been engineered to comprise a heterologous nucleotide sequence.

In some embodiments, the single-cell-derived clones are semi-attached or loosely attached on the substrate of the present disclosure.

In some embodiments, no cell debris is observed in the cell culture system after 7 or more days of cultivation.

In some embodiments, the culturing step occurs over a period of 2-8 days (e.g., 2, 3, 4, 5, 6, 7, or 8 days). In other embodiments, the culturing step culturing step occurs over a period of 7-14 days (e.g., 7, 8, 9, 10, 11, 12, 13, or 14 days). In other embodiments, the culturing step culturing step occurs over a period of 1-4 weeks (e.g., 1, 2, 3, or 4 weeks).

In some embodiments, the single-cell-derived clone forms a single-cell-derived spheroid. In some embodiments, the single-cell-derived clone has a diameter of from about 40 µm to about 200 µm. In some embodiments, the single-cell-derived clone has a diameter of from about 50 µm to about 150 µm. In some cases, the single-cell-derived clone has a diameter of from about 50 µm to about 120 µm, from about 50 µm to about 100 µm, from about 50 µm to about 80 µm, from about 50 µm to about 60 µm, from about 80 µm to about 150 µm, from about 80 µm to about 120 µm, from about 80 µm to about 100 µm, from about 100 µm to about 200 µm, from about 100 µm to about 150 µm, or from about 100 µm to about 120 µm.

In some instances, the single-cell-derived clones form a single-cell-derived spheroid. In some cases, the spheroid comprises from about 8 to about 1000 cells. In some cases, the spheroid comprises from about 8 to about 800 cells, from about 8 to about 500 cells, from about 8 to about 400 cells, from about 8 to about 300 cells, from about 8 to about 200 cells, from about 8 to about 100 cells, from about 10 to about 1000 cells, from about 10 to about 800 cells, from about 10 to about 500 cells, from about 10 to about 400 cells, from about 10 to about 300 cells, from about 10 to about 200 cells, from about 10 to about 100 cells, from about 50 to about 1000 cells, from about 50 to about 800 cells, from about 50 to about 500 cells, from about 50 to about 400 cells, from about 50 to about 300 cells, from about 50 to about 200 cells, from about 100 to about 1000 cells, from about 100 to about 800 cells, from about 100 to about 500 cells, from about 100 to about 400 cells, from about 100 to about 300 cells, from about 300 to about 1000 cells, from about 300 to about 800 cells, from about 300 to about 500 cells, from about 500 to about 1000 cells, or from about 500 to about 800 cells.

In some embodiments, at least 10% of the cells disposed on the substrate forms single-cell-derived spheroids. In some embodiments, at least 20% of the cells disposed on the substrate forms single-cell-derived spheroids. In some embodiments, at least 30% of the cells disposed on the substrate forms single-cell-derived spheroids. In some embodiments, at least 40% of the cells disposed on the substrate forms single-cell-derived spheroids. In some embodiments, at least 50% of the cells disposed on the substrate forms single-cell-derived spheroids. In some embodiments, at least 60% of the cells disposed on the substrate forms single-cell-derived spheroids. In some embodiments, at least 70% of the cells disposed on the substrate forms single-cell-derived spheroids.

In some embodiments, the method described herein further comprises analyzing the single-cell-derived clone, thereby obtaining a characteristic of the single cell. In some instances, the step of analyzing the single-cell-derived clone comprises subjecting the single-cell-derived clone to sequencing analysis. In some embodiments, the analyzing step comprises performing a genotyping analysis. In some embodiments, the genotyping analysis is a PCR-based analysis. In some embodiments, the genotyping analysis is an array hybridization-based analysis. In some embodiments, the analyzing step comprises analyzing a copy number variation. In some embodiments, the analyzing step comprises analyzing a genetic mutation. In some embodiments, the analyzing step comprises analyzing a single nucleotide polymorphism.

In some embodiments, the step of analyzing the single-cell-derived clone comprises subjecting the single-cell-derived clone to proteomic analysis. Exemplary proteomic analysis include gel electrophoresis such as polyacrylamide gel electrophoresis (PAGE), sodium dodecyl sulfate polyacrylamide gel electrophoresis (SDS-PAGE), two-dimensional gel electrophoresis, or capillary electrophoresis; high-performance liquid chromatography (HPLC); and affinity chromatography.

In some embodiments, the characteristic of the single cell comprises one or more of: a genotype, an epigenetic profile, an expression level of a gene or a protein, a response to a drug, a drug resistance profile, or a metastatic potential.

In some aspects, provided herein is a single-cell-derived clone generated according to any one of the culture methods employing the cell culture systems described herein. In some aspects, there is provided a library of single-cell-derived clones derived according to any one of the culture methods employing the cell culture systems described herein.

Kits

In certain embodiments, disclosed herein is a kit or article of manufacture that comprises a cell culture substrate described herein. In some instances, the kit further comprises a package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

In some cases, the kit further comprises labels listing contents and/or instructions for use, and package inserts with instructions for use, e.g., instructions for culturing a heterogeneous population of cells using a cell culture substrate described herein to obtain a plurality of cell clones comprising a single-cell-derived clone. A set of instructions will also typically be included.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the term "comprising" is intended to mean that the methods include the recited steps or elements, but do not exclude others. "Consisting essentially of" shall mean rendering the claims open only for the inclusion of steps or elements, which do not materially affect the basic and novel characteristics of the claimed methods. "Consisting of" shall mean excluding any element or step not specified in the claim. Embodiments defined by each of these transition terms are within the scope of this disclosure.

As used herein, the term "positively charged polyelectrolyte" encompasses a plurality of monomer units or a non-polymeric molecule that comprises two or more positive charges. In some instances, the positively charged polyelectrolyte also encompasses a plurality of monomer units or a non-polymeric molecule that comprise charge positive groups, charge neutral groups, or charge negative groups, with a net charge of being positive.

As used herein, the term "cationic polymer" encompasses a plurality of monomer units or a non-polymeric molecule. In some instances, the cationic polymer is a synthetic polymer. In other instances, the cationic polymer is a natural polymer.

As used herein, the term "cationic polypeptide" refers to a polypeptide comprising two or more positive charges. In some instances, the cationic polypeptide comprises positively charged amino acid residues, negatively charged residues, and polar residues but the net charge of the polypeptide is positive. In some cases, the cationic polypeptide is from 8 to 100 amino acids in length. In some cases, the cationic polypeptide is from 8 to 80, 8 to 50, 8 to 40, 8 to 30, 8 to 25, 8 to 20, 8 to 15, 10 to 100, 10 to 80, 10 to 50, 10 to 40, 10 to 30, 10 to 20, 20 to 100, 20 to 80, 20 to 50, 20 to 40, 20 to 30, 30 to 100, 30 to 80, 30 to 50, 40 to 100, 40 to 80, or 50 to 100 amino acids in length.

As used herein, the term "negatively charged polyelectrolyte" encompasses a plurality of monomer units or a non-polymeric molecule that comprises two or more negative charges. In some instances, the negatively charged polyelectrolyte also encompasses a plurality of monomer units or a non-polymeric molecule that comprise charge positive groups, charge neutral groups, or charge negative groups, with a net charge of being negative.

As used herein, the term "anionic polymer" encompasses a plurality of monomer units or a non-polymeric molecule. In some instances, the anionic polymer is a synthetic polymer. In other instances, the anionic polymer is a natural polymer.

As used herein, the term "anionic polypeptide" refers to a polypeptide comprising two or more negative charges. In some instances, the anionic polypeptide comprises positively charged amino acid residues, negatively charged residues, and polar residues but the net charge of the polypeptide is negative. In some cases, the anionic polypeptide is from 8 to 100 amino acids in length. In some cases, the anionic polypeptide is from 8 to 80, 8 to 50, 8 to 40, 8 to 30, 8 to 25, 8 to 20, 8 to 15, 10 to 100, 10 to 80, 10 to 50, 10 to 40, 10 to 30, 10 to 20, 20 to 100, 20 to 80, 20 to 50, 20 to 40, 20 to 30, 30 to 100, 30 to 80, 30 to 50, 40 to 100, 40 to 80, or 50 to 100 amino acids in length.

As used herein, the term "absorbent polymer" encompasses a plurality of monomer units or a non-polymeric molecule that comprise one or more hydrophilic groups. In some instances, the absorbent polymer is permeable to an aqueous solution. In other instances, the absorbent polymer is impermeable or does not absorb the aqueous solution. In some cases, the absorbent polymer encompasses a non-reactive polymer, or a polymer that does not contain a reactive group, e.g., a group that forms covalent bonds with another compound.

As used herein, the term "polymer" includes both homo- and copolymers, branched and unbranched, and natural or synthetic polymers.

As used herein, the term "elastomer" refers to a polymer with viscoelastic properties, low crystallinity, and high amorphous content. In some instances, the elastomer has a low Young's modulus and high elongation at break compared to other materials. In some cases, elastomers are amorphous polymers generated from monomers of carbon, hydrogen, oxygen, and/or silicon.

As used herein, immune cells encompass neutrophils, eosinophils, basophils, mast cells, monocytes, macrophages, dendritic cells, natural killer cells, and lymphocytes (B cells and T cells).

Endothelial cells are cells that line the interior surface of blood vessels and lymphatic vessels. Exemplary endothelial cells include high endothelial venules (HEV), endothelium of the bone marrow, and endothelium of the brain.

Epithelial cells are cells that line the outer surfaces of organs and blood vessels, and the inner surfaces of cavities within internal organs. Exemplary epithelial cells include squamous epithelium, cuboidal epithelium, and columnar epithelium.

As used herein, the term "stem cell" encompasses an adult stem cell and an embryonic stem cell. Exemplary stem cells include hematopoietic stem cells, mesenchymal stem cells (MSCs), neural stem cells, epithelial stem cells, skin stem cells, embryonic stem cells (ESCs), and induced pluripotent stem cells (iPSCs).

EXAMPLES

These examples are provided for illustrative purposes only and not to limit the scope of the claims provided herein.

Example 1: Construction of the Substrate of the Invention

Preparation of PDMS Having a Hydrophobic Surface

The procedure for preparing a PDMS with a hydrophobic surface consists in mixing PDMS mixture consisting of the PDMS monomer A and a curing agent B (Sylgard 184 silicone elastomer kit, Dow Corning) at a 10:1 (w/w) ratio. The mixture is poured into a Petri dish and cured at 70° C. for 15 h. The resulting PDMS membrane, about 1 mm thick, is hydrophobic.

Any suitable PDMS hydrophilic surface modification may be employed to convert the hydrophobic surface to a hydrophilic surface. The followings are exemplary embodiments of PDMS hydrophilic surface modifications.

Hydrophilic Surface Modification of PDMS Via PVA Deposition

The first step in the treatment is to expose the PDMS surface to an oxygen plasma, followed by exposing plasma oxidized PDMS surfaces to 1-2 wt % PVA in water for a short period of time (e.g., 10 min). Oxygen plasma treatment generates radical species of surface silanol groups (Si—OH), alcoholic hydroxyls (C—OH), and carboxylic acids (COOH) on the PDMS surface and these species allow hydrogen bonding between the PVA molecules and the activated PDMS surfaces, which leads to permanently hydrophilized surfaces. The PVA-treated PDMS surfaces retain the hydrophilicity in the long term.

Contact angle measurements can be applied to examine the effect of PVA deposition on PDMS surface properties. The PDMS treated with plasma and PVA shows lower water-air contact angles than untreated PDMS. The surface roughness of the plasma oxidized PDMS surfaces with a PVA coating is higher than that of the untreated PDMS surface.

Figure 6:
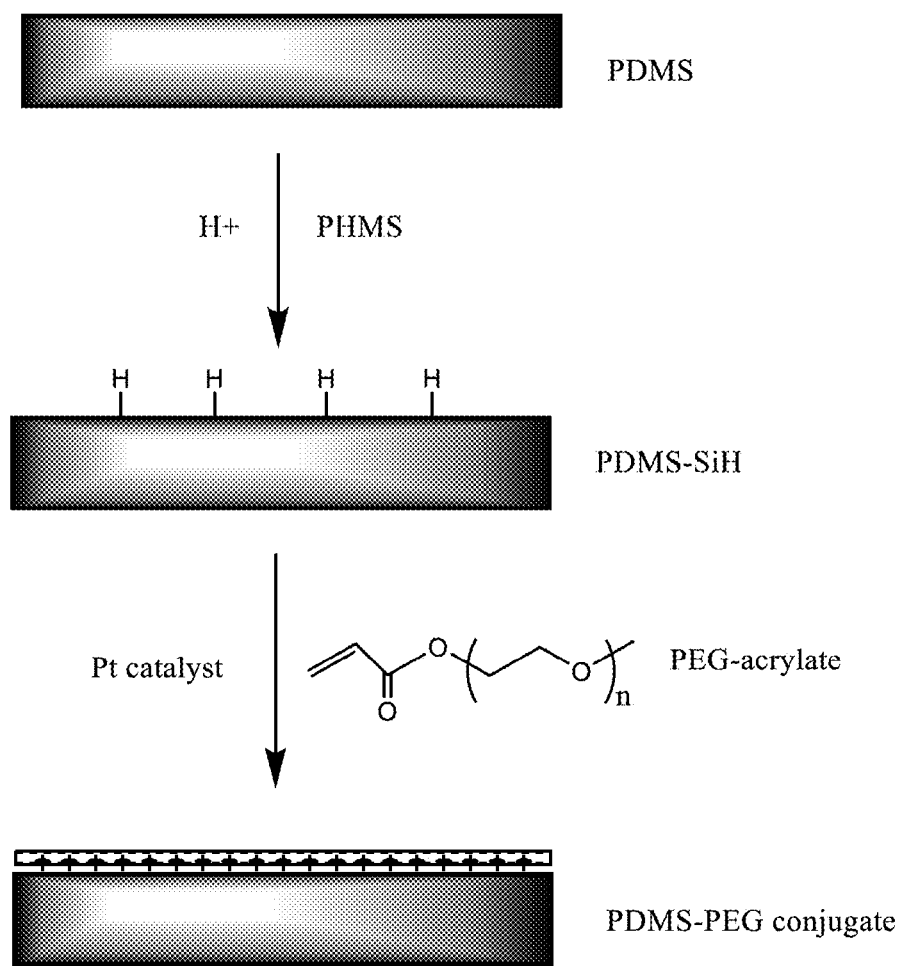
FIG. 6 illustrates the reaction scheme of the surface modification of PDMS. The first step is to introduce SiH groups onto the PDMS surface (PDMS-SiH). The second step involves in the formation of a PEG-PDMS conjugate.

Hydrophilic Surface Modification of PDMS Via Hydrosilylation and PEG Conjugation FIG. 6 illustrates an exemplary hydrophilic surface modification of PDMS via hydrosilylation. Poly(ethylene glycol) methyl ether acrylate (PEG-acrylate) can be used to modify the hydrophobic surface of PDMS through covalent bonding of PEG-acrylate chains on the PDMS surface. The incorporation of SiH groups on the PDMS surfaces involves exchanging $Me_2SiO$ of PDMS with HMeSiO of PHMS using acid catalysis. This leads to PDMS with a high concentration of SiH groups on its surface.

The first step in the treatment is to introduce SiH groups onto the PDMS surface (PDMS-SiH) by immersing the PDMS in polyhydromethylsiloxane (PHMS) with methanol. A catalystic amount of trifluoromethanesul-fonic acid is added and the system is set for about 30 min at room temperature. PDMS surface is then rinsed sequentially in solvents (e.g., methanol, hexane) to remove residual reactants, and dried under vacuum.

The second step in the treatment is to prepare PEG modified PDMS surface by introducing the PDMS-SiH sample to a mixture of PEG-acrylate and diethylene-glycol dimethyl ether (1:3, v/v). A catalytic amount of Karstedt's catalyst (platinum-divinyltetramethyldisiloxane complex) is added to the reaction mixture, and stirred at 70.0 for a sufficient reaction time. Modified PDMS surface exhibits lower water-air contact angle and higher surface energy than untreated PDMS.

Buildup of Polyelectrolyte Multilayers

PLL (MW 150K-300K), PLGA (MW 50K-100K), PLO (0.01%) solution, PLH (MW 5K-25K), PLA (MW 15K-70K) are commercially available from Sigma-Aldrich (St.

Louis, Mo., USA). Both polycation and polyanion are dissolved in Tris-HCl buffer (pH 7.4) and deposited onto the PVA or PEG coated surface after rinsing with Tris-HCl buffer. Each layer of polycation or polyanion is deposited and incubated for 10 min, followed by washing with Tris-HCl buffer 3 times for 2, 1, and 1 min. The PLL/PLGA, PLO/PLGA, PLH/PLGA and PLA/PLGA multilayer films can be fabricated by layer-by-layer self-assembly onto the PVA or PEG coated surface as follows.

PLL/PLGA Multilayers

In some embodiments, the polyelectrolyte multilayers are PLL/PLGA multilayers that can be constructed by sequentially depositing PLL and PLGA on the surface of PVA/PDMS or PEG/PDMS. Each depositing step comprises adding the PLL or PLGA solution to the plate surface, incubated for 10 min and washed 3 times for 2, 1, and 1 min.

In one embodiment, the substrate composed of $(PLGA/PLL)_3$/PVA/PDMS is constructed. In one embodiment, the substrate coating composed of $(PLGA/PLL)_5$/PVA/PDMS is constructed. In one embodiment, the substrate composed of $(PLGA/PLL)_{10}$/PVA/PDMS is constructed. In one embodiment, the substrate composed of $(PLGA/PLL)_{15}$/PVA/PDMS is constructed. In one embodiment, the substrate composed of PLL $(PLGA/PLL)_3$/PVA/PDMS is constructed. In one embodiment, the substrate composed of PLL $(PLGA/PLL)_5$/PVA/PDMS is constructed. In one embodiment, the substrate composed of PLL $(PLGA/PLL)_{10}$/PVA/PDMS is constructed. In one embodiment, the substrate composed of PLL $(PLGA/PLL)_{15}$/PVA/PDMS is constructed. In one embodiment, the substrate composed of $(PLGA/PLL)_3$/PEG/PDMS is constructed. In one embodiment, the substrate coating composed of $(PLGA/PLL)_5$/PEG/PDMS is constructed. In one embodiment, the substrate composed of $(PLGA/PLL)_{10}$/PEG/PDMS is constructed. In one embodiment, the substrate composed of $(PLGA/PLL)_{15}$/PEG/PDMS is constructed. In one embodiment, the substrate composed of PLL $(PLGA/PLL)_3$/PEG/PDMS is constructed. In one embodiment, the substrate composed of PLL $(PLGA/PLL)_5$/P PEG/PDMS is constructed. In one embodiment, the substrate composed of PLL $(PLGA/PLL)_{10}$/PEG/PDMS is constructed. In one embodiment, the substrate composed of PLL $(PLGA/PLL)_{15}$/PEG/PDMS is constructed.

PLO/PLGA Multilayers

In some embodiments, the polyelectrolyte multilayers are PLO/PLGA multilayers that can be constructed by sequentially depositing PLO and PLGA on the surface of PVA/PDMS or PEG/PDMS. Each depositing step comprises adding the PLO or PLGA solution to the plate surface, incubated for 10 min and washed 3 times for 2, 1, and 1 min.

In one embodiment, the substrate composed of $(PLGA/PLO)_3$/PVA/PDMS is constructed. In one embodiment, the substrate coating composed of $(PLGA/PLO)_5$/PVA/PDMS is constructed. In one embodiment, the substrate composed of $(PLGA/PLO)_{10}$/PVA/PDMS is constructed. In one embodiment, the substrate composed of $(PLGA/PLO)_{15}$/PVA/PDMS is constructed. In one embodiment, the substrate composed of PLO $(PLGA/PLO)_3$/PVA/PDMS is constructed. In one embodiment, the substrate composed of PLO $(PLGA/PLO)_5$/PVA/PDMS is constructed. In one embodiment, the substrate composed of PLO $(PLGA/PLO)_{10}$/PVA/PDMS is constructed. In one embodiment, the substrate composed of PLO $(PLGA/PLO)_{15}$/PVA/PDMS is constructed. In one embodiment, the substrate composed of $(PLGA/PLO)_3$/PEG/PDMS is constructed. In one embodiment, the substrate coating composed of $(PLGA/PLO)_5$/PEG/PDMS is constructed. In one embodiment, the substrate composed of $(PLGA/PLO)_{10}$/PEG/PDMS is constructed. In one embodiment, the substrate composed of $(PLGA/PLO)_{15}$/PEG/PDMS is constructed. In one embodiment, the substrate composed of PLO $(PLGA/PLO)_3$/PEG/PDMS is constructed. In one embodiment, the substrate composed of PLO $(PLGA/PLO)_5$/P PEG/PDMS is constructed. In one embodiment, the substrate composed of PLO $(PLGA/PLO)_{10}$/PEG/PDMS is constructed. In one embodiment, the substrate composed of PLO $(PLGA/PLO)_{15}$/PEG/PDMS is constructed.

PLH/PLGA Multilayers

In some embodiments, the polyelectrolyte multilayers are PLH/PLGA multilayers that can be constructed by sequentially depositing PLH and PLGA on the surface of PVA/PDMS or PEG/PDMS. Each depositing step comprises adding the PLH or PLGA solution to the plate surface, incubated for 10 min and washed 3 times for 2, 1, and 1 min.

In one embodiment, the substrate composed of $(PLGA/PLH)_3$/PVA/PDMS is constructed. In one embodiment, the substrate coating composed of $(PLGA/PLH)_5$/PVA/PDMS is constructed. In one embodiment, the substrate composed of $(PLGA/PLH)_{10}$/PVA/PDMS is constructed. In one embodiment, the substrate composed of $(PLGA/PLH)_{15}$/PVA/PDMS is constructed. In one embodiment, the substrate composed of PLH $(PLGA/PLH)_3$/PVA/PDMS is constructed. In one embodiment, the substrate composed of PLH $(PLGA/PLH)_5$/PVA/PDMS is constructed. In one embodiment, the substrate composed of PLH $(PLGA/PLH)_{10}$/PVA/PDMS is constructed. In one embodiment, the substrate composed of PLH $(PLGA/PLH)_{15}$/PVA/PDMS is constructed. In one embodiment, the substrate composed of $(PLGA/PLH)_3$/PEG/PDMS is constructed. In one embodiment, the substrate coating composed of $(PLGA/PLH)_5$/PEG/PDMS is constructed. In one embodiment, the substrate composed of $(PLGA/PLH)_{10}$/PEG/PDMS is constructed. In one embodiment, the substrate composed of $(PLGA/PLH)_{15}$/PEG/PDMS is constructed. In one embodiment, the substrate composed of PLH $(PLGA/PLH)_3$/PEG/PDMS is constructed. In one embodiment, the substrate composed of PLH $(PLGA/PLH)_5$/P PEG/PDMS is constructed. In one embodiment, the substrate composed of PLH $(PLGA/PLH)_{10}$/PEG/PDMS is constructed. In one embodiment, the substrate composed of PLH $(PLGA/PLH)_{15}$/PEG/PDMS is constructed.

PLA/PLGA Multilayers

In some embodiments, the polyelectrolyte multilayers are PLA/PLGA multilayers that can be constructed by sequentially depositing PLA and PLGA on the surface of PVA/PDMS or PEG/PDMS. Each depositing step comprises adding the PLA or PLGA solution to the plate surface, incubated for 10 min and washed 3 times for 2, 1, and 1 min.

In one embodiment, the substrate composed of $(PLGA/PLA)_3$/PVA/PDMS is constructed. In one embodiment, the substrate coating composed of $(PLGA/PLA)_5$/PVA/PDMS is constructed. In one embodiment, the substrate composed of $(PLGA/PLA)_{10}$/PVA/PDMS is constructed. In one embodiment, the substrate composed of $(PLGA/PLA)_{15}$/PVA/PDMS is constructed. In one embodiment, the substrate composed of PLA $(PLGA/PLA)_3$/PVA/PDMS is constructed. In one embodiment, the substrate composed of PLA $(PLGA/PLA)_5$/PVA/PDMS is constructed. In one embodiment, the substrate composed of PLA $(PLGA/PLA)_{10}$/PVA/PDMS is constructed. In one embodiment, the substrate composed of PLA $(PLGA/PLA)_{15}$/PVA/PDMS is constructed. In one embodiment, the substrate composed of $(PLGA/PLA)_3$/PEG/PDMS is constructed. In one embodiment, the substrate coating composed of $(PLGA/PLA)_5$/

PEG/PDMS is constructed. In one embodiment, the substrate composed of (PLGA/PLA)$_{10}$/PEG/PDMS is constructed. In one embodiment, the substrate composed of (PLGA/PLA)$_{15}$/PEG/PDMS is constructed. In one embodiment, the substrate composed of PLA (PLGA/PLA)$_3$/PEG/PDMS is constructed. In one embodiment, the substrate composed of PLA (PLGA/PLA)$_5$/P PEG/PDMS is constructed. In one embodiment, the substrate composed of PLA (PLGA/PLA)$_{10}$/PEG/PDMS is constructed. In one embodiment, the substrate composed of PLA (PLGA/PLA)$_{15}$/PEG/PDMS is constructed.

Quartz Crystal Microbalance-Dissipation (QCM-D) Measurement

QCM experiments were performed under Q-Sense E4 (Biolin Scientific AB/Q-sence, Sweden). The silicon oxide (SiO$_2$) coated quartz crystal chips (AT-cut quartz crystals, f0=5 MHz) were cleaned in 0.1M sodium dodecyl sulfate, followed by rinsing with Milli-Q water, drying under nitrogen, and exposing to oxygen plasma for 20 seconds. For QCM-D measurement, the chamber was stabilized to 25 degree C. and all measurements were recorded at the third overtone (15 MHz). To simulate the serial surface coating, the concentration and the washing conditions of each coating step in the QCM-D chamber are identical. About 1% bovine serum albumin (BSA, Millipore, Bedford, Mass.) was used for non-specific adsorption investigation and was introduced to chambers on the surface.

Surface Chemical Analysis

The chemical composition of the surface coating of the present disclosure was analyzed by X-ray photoelectron spectroscopy (XPS; VersaProbe III, PHI) with C60 (10 kV, 10 nA) etching on silicon wafer. The pass energy used was 93.9 eV at steps of 0.5 eV. The relative atomic concentrations of carbon, nitrogen, oxygen and silicon were measured in the layer of samples to a maximum thickness of 10 nm.

Surface Roughness Measurement by Using Atomic-Force Microscope (AFM)

The roughness of the surface coating of the present disclosure was measured using atomic force microscope (AFM; Nanowizard 3, JPK instrument) with tapping mode. Silicon cantilevers with a resonant frequency of 134 kHz were utilized for the experiments.

Example 2: Formation of Single-Cell Derived Spheroids

Figure 7:
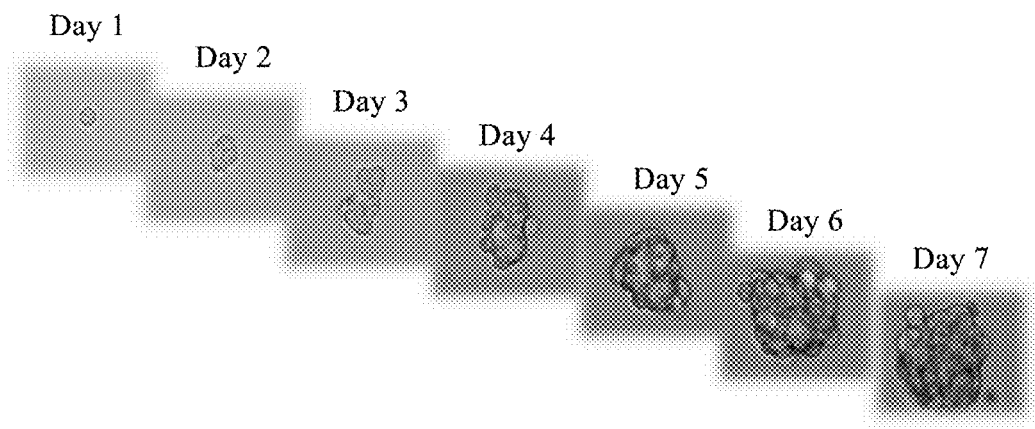
FIG. 7 shows the time-lapse microscope observation of HCT116 colorectal cancer cells cultured on the substrate of the invention on day 1, 2, 3, 4, 5, 6 and 7 during the growth of the cancer cells supplied with complete DMEM medium. (Image photographed by Leica DMI6000B time-lapse microscope under 10× objective).

FIG. 7 shows the time-lapse microscope observation of HCT116 colorectal cancer cells cultured on the substrate of the invention on day 1, 2, 3, 4, 5, 6 and 7 during the growth of the cancer cells supplied with complete DMEM medium. (Image photographed by Leica DMI6000B time-lapse microscope under 10× objective).

Example 3: Generation of Cell Line-Derived Tumor Spheroids

Figures 8A, 8B, 8C:
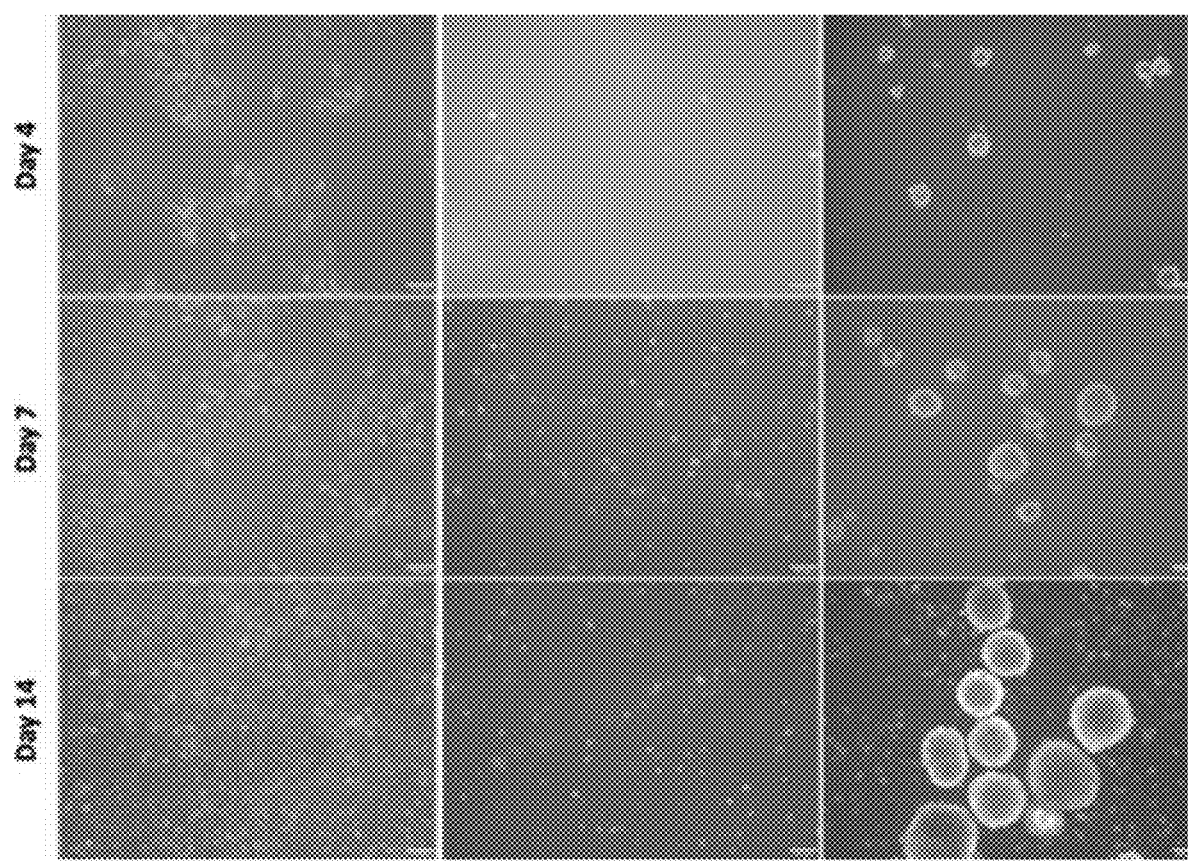
FIGS. 8A-8C show the results of ex vivo cultivation of HCT116 colorectal cancer cell on various culture plates for 4, 7 and 14 days. (A) A tissue culture plate (TCP), (B) a culture plate comprising PVA/PDMS coated surface, and (C) a culture plate comprising (PLL/PLGA)$_{15}$/PVA/PDMS coated surface. Cells are adhesive on TCP and the PVA/PDMS coated surface whereas the cells form spheroids on the (PLL/PLGA)$_{15}$/PVA/PDMS coated surface.
Figure 9A:
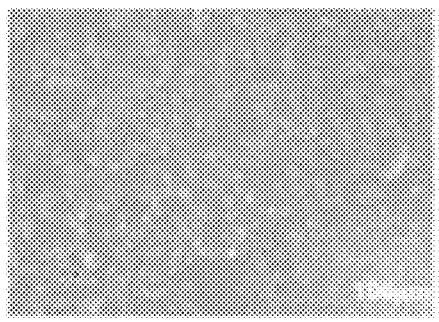
FIGS. 9A-9D show the results of ex vivo cultivation of patient-derived clinical samples: (A) breast cancer cells from a needle biopsy grown on a tissue culture plate (TCP) for 2 weeks, (B) breast cancer cells from a needle biopsy grown on the substrate of the invention for 2 weeks, (C) urothelial cancer cells from a tumor tissue grown on the substrate of the invention for 2 weeks, (D) colorectal cancer cells from a tumor tissue grown on the substrate of the invention for 2 weeks.
Figure 9B:
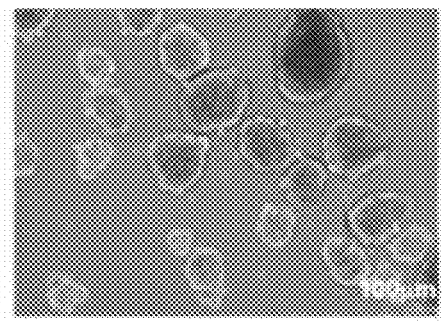
Figure 9C:
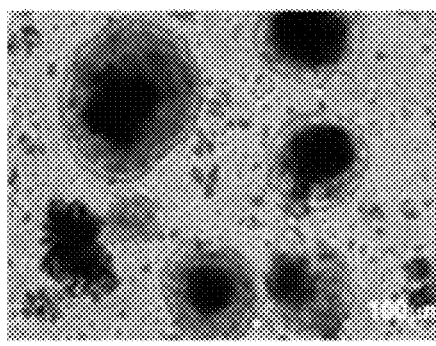
Figure 9D:
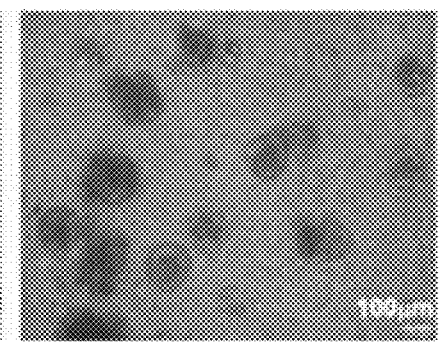

The substrate of the present disclosure provides a biocompatible multilayer coated surface that enables cell adhesion for cell proliferation, and also provides non-fouling characteristic for spheroid formation directly on the surface. For comparison, FIGS. 8A-8C show the results of ex vivo cultivation of HCT116 colorectal cancer cell on various culture plates for 4, 7 and 14 days. (A) A tissue culture plate (TCP), (B) a culture plate comprising PVA/PDMS coated surface, and (C) a culture plate comprising (PLL/PLGA)$_{15}$/PVA/PDMS coated surface. Cells are adhesive on TCP and the PVA/PDMS coated surface whereas the cells form spheroids (i.e., tumor spheroids) on the (PLL/PLGA)$_{15}$/PVA/PDMS coated surface.

Example 4: Generation of Patient-Derived Tumor Spheroids

The cell culture system comprising the substrate of the present disclosure was tested with various patient-derived clinical samples and resulted in the successful cultivation and formation of spheroids. FIGS. 9A-9D show the results of ex vivo cultivation of patient-derived clinical samples: (A) breast cancer cells from a needle biopsy grown on a tissue culture plate (TCP) for 2 weeks, (B) breast cancer cells from a needle biopsy grown on the substrate of the invention for 2 weeks, (C) urothelial cancer cells from a tumor tissue grown on the substrate of the invention for 2 weeks, (D) colorectal cancer cells from a tumor tissue grown on the substrate of the invention for 2 weeks.

The spheroids generated thereof may further benefit for future diagnosis and guidance in medical treatment and application, ex: non-invasive early cancer detection, personal medicine guidance, pre- and post-treatment drug resistance investigation, cell activity evaluation for immune cell-based cancer therapy, and provide substantial material to elucidate the mechanism participated in cancer progression by using the ex vivo cultivated patient-derived primary CTC cells.

Example 5: Generation of Human-Derived Spheroids

Figure 10:
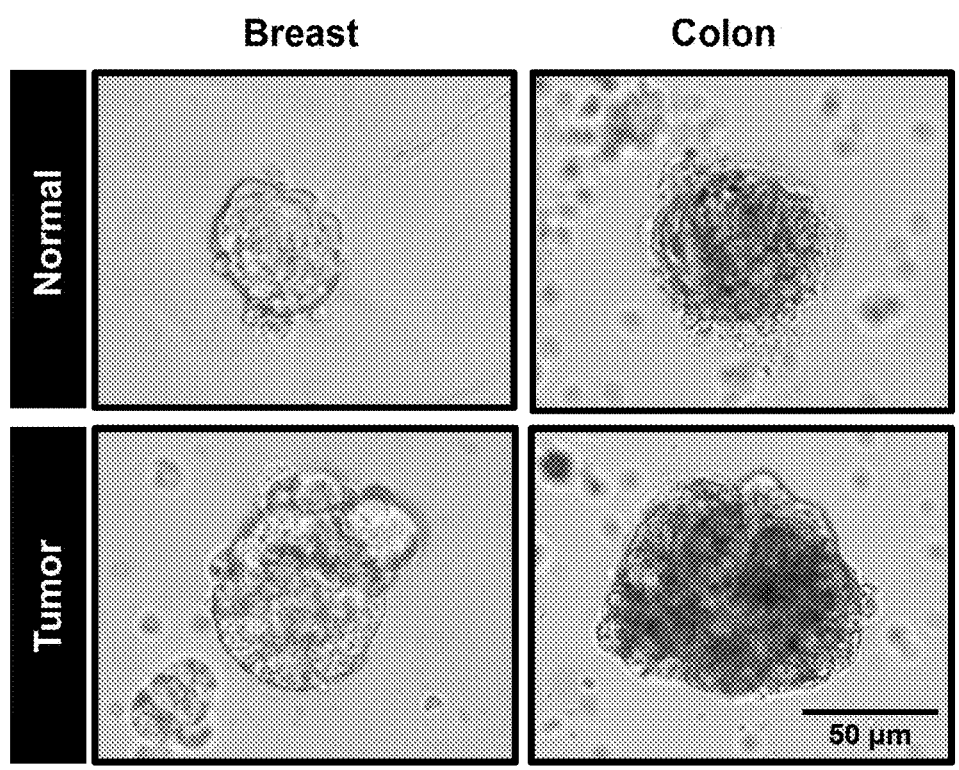
FIG. 10 show the results of ex vivo cultivation of patient-derived normal samples of breast cells and colorectal cells, and patient-derived tumor samples of breast cancer cells and colorectal cancer cells grown on the substrate of the invention for 2 weeks.

FIG. 10 show the results of ex vivo cultivation of patient-derived normal samples of breast cells and colorectal cells, and patient-derived tumor samples of breast cancer cells and colorectal cancer cells grown on the substrate of the invention for 2 weeks.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

The invention claimed is:

1. A substrate for cell culture, the substrate comprising an elastomer membrane having a surface coating comprising:
   a) an absorbent polymer, wherein the absorbent polymer is deposited on a surface of the elastomer membrane, and
   b) polyelectrolyte multilayers, wherein the absorbent polymer is in direct contact with a polycation or a polyanion of the polyelectrolyte multilayers,
wherein the elastomer membrane comprises polydimethylsiloxane (PDMS).

2. The substrate of claim 1, wherein the absorbent polymer is selected from the group consisting of poly(vinyl alcohol) (PVA), poly(ethylene glycol) (PEG), PEG-acrylate, polyvinylpyrrolidone (PVP), polyethyleneimine (PEI), poly-L-lactide (PLLA), poly-D-lactide (PDLA), poly(L-lactide-co-D,L-lactide) (PLDLLA), poly(glycolic acid) (PGA), poly(lactic-co-glycolic acid) (PL-co-GA), poly(methyl methacrylate) (PMMA), poly(hydroxyethyl methacrylate) (p-HEMA), and derivatives thereof.

3. The substrate of claim 2, wherein the absorbent polymer is PVA, PEG, PEG-acrylate, PVP, PEI, PMMA, or a derivative thereof.

4. The substrate of claim 2, wherein the absorbent polymer is PVA, PEG, or PEG-acrylate.

5. The substrate of claim 1, wherein the absorbent polymer is conjugated to the PDMS.

6. The substrate of claim 1, wherein the absorbent polymer and the PDMS are not conjugated.

7. The substrate of claim 1, wherein the polycation is a poly(amino acid).

8. The substrate of claim 1, wherein the polyanion is a poly(amino acid).

9. The substrate of claim 1, wherein the polycation is selected from the group consisting of poly(L-lysine) (PLL), poly(L-arginine) (PLA), poly(L-ornithine) (PLO), poly(L-histidine) (PLH), and a combination thereof.

10. The substrate of claim 9, wherein the polycation is PLL, PLA, PLO, or PLH.

11. The substrate of claim 1, wherein the polyanion is poly(L-glutamic acid) (PLGA), poly(L-aspartic acid) (PLAA), or a combination thereof.

12. The substrate of claim 1, wherein the polyelectrolyte multilayers comprise at least one bilayer of polycation and polyanion selected from the group consisting of PLL/PLGA, PLL/PLAA, PLA/PLGA, PLA/PLAA, PLO/PLGA, PLO/PLAA, PLH/PLGA, PLH/PLAA, and a combination thereof.

13. The substrate of claim 1, wherein the polyelectrolyte multilayers are formed via layer-by-layer assembly.

14. The substrate of claim 1, wherein the polyelectrolyte multilayers comprise n bilayers, wherein n is an integer number ranging from 1 to 30, and wherein the outermost layer is a polycation or a polyanion.

15. The substrate of claim 1, wherein the polyelectrolyte multilayers comprise n bilayers of polycation and polyanion, and an additional layer of polyanion, wherein n is an integer number ranging from 1 to 30, and wherein the outermost layer is polyanion.

16. The substrate of claim 1, wherein the polyelectrolyte multilayers comprise n bilayers of polycation and polyanion, and an additional layer of polycation, wherein n is an integer number ranging from 1 to 30, and wherein the outermost layer is polycation.

17. A method of preparing the substrate of claim 1, comprising:
   a) providing the elastomer membrane having a hydrophobic surface,
   b) modifying the hydrophobic surface of the elastomer membrane with a treatment,
   c) applying an absorbent polymer to the modified surface of the elastomer membrane, and
   d) sequentially depositing on the absorbent polymer alternating layers of polycations and polyanions to form a substrate in a form of a multilayered membrane.

18. The method of claim 17, wherein the treatment is a plasma treatment, corona discharge or UV ozone treatment.

19. The method of claim 17, wherein the treatment is a hydrosilylation.

20. The method of claim 17, wherein the hydrophobic surface of the elastomeric membrane is irradiated or hydrophilized after the treatment.

21. The method of claim 17, wherein the elastomer membrane surface is hydrophilized after applying the absorbent polymer to the modified surface.

22. The method of claim 17, wherein the absorbent polymer is PVA, PEG, or PEG-acrylate.

23. The method of claim 17, wherein the absorbent polymer is crosslinked to the elastomer membrane surface.

24. The method of claim 17, wherein the elastomer membrane is free of crosslink.

25. A cell culture system, comprising the substrate of claim 1.

26. The cell culture system of claim 25, further comprising cells and/or culture media.

27. A method for culturing cells, the method comprising:
   a) providing a cell culture system comprising the substrate of claim 1,
   b) seeding cells on the substrate, and
   c) culturing the cells under a suitable medium for a sufficient period of time to form one or more single-cell derived spheroids.

28. The method of claim 27, wherein the one or more single-cell derived spheroids are generated via single cell proliferation; or wherein the one or more spheroids have an average diameter between 50 μM and 150 μM; or wherein the seeding comprises plating the cells at a density less than 1000 cells per cm$^2$ on the substrate.

29. A method for obtaining and optionally characterizing one or more single-cell derived spheroids, comprising: (a) culturing a heterogeneous population of cells on the substrate of claim 1 to obtain at least one single-cell-derived spheroid disposed on the surface coating, wherein the single cell is a cell in the heterogeneous population of cells; and optionally (b) analyzing the single-cell-derived spheroid to thereby obtain at least one characteristic of the single cell.

30. A method for personalized drug screening, comprising: (a) culturing a plurality of cells comprising tumor cells derived from a cancer patient on the substrate of claim 1 to obtain at least one single-cell derived tumoroid disposed on the surface coating, wherein the single cell is a tumor cell in the plurality of cells; and (b) contacting the tumoroid with one or more candidate agents and detecting the presence or absence of one or more changes in the tumoroid that is indicative of therapeutic efficacy for treating the cancer.

* * * * *